US006936428B2

(12) United States Patent
Davis et al.

(10) Patent No.: US 6,936,428 B2
(45) Date of Patent: Aug. 30, 2005

(54) DIMERIC FLOURESCENT POLYPEPTIDES

(75) Inventors: Ronald W. Davis, Palo Alto, CA (US); Peter Vaillancourt, Del Mar, CA (US)

(73) Assignee: Stratagene California, La Jolla, CA (US)

( * ) Notice: Subject to any disclaimer, the term of this patent is extended or adjusted under 35 U.S.C. 154(b) by 0 days.

(21) Appl. No.: 10/021,818

(22) Filed: Dec. 13, 2001

(65) Prior Publication Data

US 2003/0108566 A1 Jun. 12, 2003

Related U.S. Application Data

(60) Provisional application No. 60/256,121, filed on Dec. 15, 2000.

(51) Int. Cl.[7] ......................... G01N 33/53; C12P 21/02; C07K 14/00; C07H 21/04

(52) U.S. Cl. ........................ 435/7.21; 435/7.1; 435/7.2; 530/350; 536/23.4

(58) Field of Search ......................... 530/350; 435/69.7, 435/7.1, 7.2, 72.21; 536/23.4

(56) References Cited

U.S. PATENT DOCUMENTS 5,981,200 A 11/1999 Tsien et al. .................. 435/7.4
5,985,577 A * 11/1999 Bulinski ........................ 435/6

FOREIGN PATENT DOCUMENTS

WO WO99/49019 9/1999 ............ C12N/9/00
WO WO00/22128 4/2000

OTHER PUBLICATIONS

NiceProt view of Swiss–Prot: P22629 (available at http://us.expasy.org/).*

Periasamy et al. (1997) nln Functional Imaging and Optical Manipulation of Living Cells, Proc. SPIE 2983, ed. DL Farkas, BJ Tromberg. Belingham, WA: SPIE, pp. 58–66.*

Swiss–Prot Database Entry P42212.*

Chalfie, et al., "Green Fluorescent Protein as a Marker for Gene Expression", 1994, Science 263: 802–805.

Tsien, "The Green Fluorescent Protein", 1998, Annual Review. Biochemistry. 67: 509–544.

Ward, et al., "Energy Transfer Proceses in Bioluminescence", 1979, Photochem. Photobiol Rev. 4: 1–57.

Wouters, et al. "Fluorescence lifetime imaging of receptor tyrosine kinase activity in cells", Curr Biol. Oct. 1999, vol. 9, No. 19, pp. 1127–1130.

Oker–Blom, et al. "Highly efficient production of GFP and its derivatives in insect cells for visual in vitro applications", FEBS Lett. Jul. 1996, vol. 389, No. 3, pp. 238–243.

Xu, et al., "Detection of programmed cell death using fluorescence energy transfer", Nucleic Acid Research. Apr. 1998, vol. 26, No. 8, pp. 2034–2035.

VonArnim, et al., "Cloninig vectors for the expression of green fluorescent protein fusion proteins in transgenic plants", Gene, Oct. 1998, vol. 221, No. 1, pp. 35–43.

Dabrowski, et al. Use of the Green Fluorescent Protein Variant (YFP) to Monitor MetArg Human Proinsulin Production in *Escherichia Coli*, Protein Expr. Purif. Jul. 1999, vol. 16, No. 2, pp. 315–323.

Luebke, K.J. "A FLASH of insight into cellular chemistry: genetically encoded labels for protein visualization in vivo", Chem & Biol. Dec. 1998, vol. 5, No. 12, pp. R317–322.

Copy of the International Search Report (PCT/US01/48690).

So, Jae–Seong, "Mini–transposon Tn5gfp Constructs for Differential Tagging of Microorganisms", Biotechnology and Bioprocess Engineering (1999), v. 4, pp. 154–156.

Copy of the Supplemental Partial European Search Report (EP01991178).

* cited by examiner

*Primary Examiner*—David Guzo
*Assistant Examiner*—Daniel M. Sullivan
(74) *Attorney, Agent, or Firm*—Palmer & Dodge LLP; Kathleen M. Williams; Mark J. FitzGerald

(57) ABSTRACT

The invention relates to proteins or polypeptides that comprise intramolecular dimers of fluorescent protein monomers. More specifically, the invention relates to recombinant polypeptides comprising a monomer of a fluorescent polypeptide, a linker peptide, and a second monomer of that fluorescent polypeptide, where the monomers form an intramolecular dimer. The invention also relates to nucleic acids encoding Intramolecular Dimer Fluorescent Proteins (IDFPs) and vectors comprising such nucleic acids. The invention further relates to methods of making IDFPs and methods of using them. IDFPs are, useful in any application suited for fluorescent proteins and are particularly useful in applications in which more than one fluorescent protein sharing complementary dimerization interfaces is present in the same mixture or is expressed in the same cell, because IDFPs do not form heterodimers.

18 Claims, 5 Drawing Sheets

FIGURE 1. RENILLA RENIFORMIS POLYNUCLEOTIDE SEQUENCE (SEQ ID NO.1)

*R. ren*: 1 ATGGTGAGTAAACAAATATTGAAGAACACTGGATTGCAGGAGATCATGTCGTTTAAAGTGAATC 64

*R. ren*: 65 TGGAAGGTGTAGTAAACAATCATGTGTTCACAATGGAAGGTTGTGGAAAAGGAAATATTT 124

*R. ren*: 125 TATTCGGAAACCAACTGGTTCAGATTCGTGTCACAAAAGGGGCTCCGCTTCCATTTGCAT 184

*R. ren*: 185 TTGATATTCTCTCACCAGCTTTCCAATACGGCAACCGTACATTCACGAAATACCCGGAGG 244

*R. ren*: 245 ATATATCAGACTTTTTTATACAATCATTTCCAGCGGGATTTGTATACGAAAGAACGTTGC 304

*R. ren*: 305 GTTACGAAGATGGTGGACTGGTTGAAATCCGTTCAGATATAAATTTAATCGAGGAGATGT 364

*R. ren*: 365 TTGTCTACAGAGTGGAATATAAAGGTAGTAACTTCCCGAATGATGGTCCAGTGATGAAGA 424

*R. ren*: 425 AGACAATCACAGGATTACAACCTTCGTTCGAAGTTGTGTATATGAACGATGGCGTCTTGG 484

*R. ren*: 485 TTGGCCAAGTCATTCTTGTTTATAGATTAAACTCTGGCAAATTTTATTCGTGTCACATGA 544

*R. ren*: 545 GAACACTGATGAAATCAAAGGGTGTAGTGAAGGATTTTCCCGAATACCATTTCATTCAAC 604

*R. ren*: 605 ATCGTTTAGAGAAGACGTATGTGGAAGACGGAGGTTTTGTTGAGCAACACGAGACGGCCA 664

*R. ren*: 665 TTGCTCAACTGACATCGCTGGGGAAACCACTTGGATCCTTACACGAATGGGTTTAA 720

FIGURE 2. RENILLA RENIFORMIS AMINO ACID SEQUENCE
(SEQ ID NO:2)

*R. reni*: 1 MSKQILKNTGLQEIMSFKVNLEGVVNNHVFTMEGCGKGNILFGNQLVQIRVTKGAPLPFA 60

*R. reni*: 61 FDILSPAFQYGNRTFTKYPEDISDFFIQSFPAGFVYERTLRYEDGGLVEIRSDINLIEQM 120

*R. reni*: 121 FVYRVEYKGSNFPNDGPVMKKTITGLQPSFEVVYMNDGVLVGQVILVYRLNSGKFYSCHM 181

*R. reni*: 182 RTLMKSKGVVKDFPEYHFIQHRLEKTYVEDGGFVEQHETAIAQLTSLGKPLGSLHEWV 238

FIGURE 3. POLYNUCLEOTIDE AND AMINO ACID SEQUENCES OF A HUMANIZED *R. RENIFORMIS* GFP. (SEQ ID NOs: 3 and 4, respectively)

```
1   ATGGTGAGCAAGCAGATCCTGAAGAACACCGGCCTGCAGGAGATCATGAGCTTCAAGGTG
     M  V  S  K  Q  I  L  K  N  T  G  L  Q  E  I  M  S  F  K  V

61  AACCTGGAGGGCGTGGTGAACAACCACGTGTTCACCATGGAGGGCTGCGGCAAGGGCAAC
     N  L  E  G  V  V  N  N  H  V  F  T  M  E  G  C  G  K  G  N

121 ATCCTGTTCGGCAACCAGCTGGTGCAGATCCGCGTGACCAAGGGCGCCCCCCTGCCCTTC
     I  L  F  G  N  Q  L  V  Q  I  R  V  T  K  G  A  P  L  P  F

181 GCCTTCGACATCCTGAGCCCCGCCTTCCAGTACGGCAACCGCACCTTCACCAAGTACCCC
     A  F  D  I  L  S  P  A  F  Q  Y  G  N  R  T  F  T  K  Y  P

241 GAGGACATCAGCGACTTCTTCATCCAGAGCTTCCCCGCCGGCTTCGTGTACGAGCGCACC
     E  D  I  S  D  F  F  I  Q  S  F  P  A  G  F  V  Y  E  R  T

301 CTGCGCTACGAGGACGGCGGCCTGGTGGAGATCCGCAGCGACATCAACCTGATCGAGGAG
     L  R  Y  E  D  G  G  L  V  E  I  R  S  D  I  N  L  I  E  E

361 ATGTTCGTGTACCGCGTGGAGTACAAGGGCCGCAACTTCCCCAACGACGGCCCCGTGATG
     M  F  V  Y  R  V  E  Y  K  G  S  N  F  P  N  D  G  P  V  M

421 AAGAAGACCATCACCGGCCTGCAGCCCAGCTTCGAGGTGGTGTACATGAACGACGGCGTG
     K  K  T  I  T  G  L  Q  P  S  F  E  V  V  Y  M  N  D  G  V

481 CTGGTGGGCCAGGTGATCCTGGTGTACCGCCTGAACAGCGGCAAGTTCTACAGCTGCCAC
     L  V  G  Q  V  I  L  V  Y  R  L  N  S  G  K  F  Y  S  C  H

544 ATGCGCACCCTGATGAAGAGCAAGGGCGTGGTGAAGGACTTCCCCGAGTACCACTTCATC
     M  R  T  L  M  K  S  K  G  V  V  K  D  F  P  E  Y  H  F  I

604 CAGCACCGCCTGGAGAAGACCTACGTGGAGGACGGCGGCTTCGTGGAGCAGCACGAGACC
     Q  H  R  L  E  K  T  Y  V  E  D  G  G  F  V  E  Q  H  E  T

664 GCCATCGCCCAGCTGACCAGCCTGGGCAAGCCCCTGGGCAGCCTGCACGAGTGGGTGTAA
     A  I  A  Q  L  T  S  L  G  K  P  L  G  S  L  H  E  W  V  -
```

A. Gly-Gly-Gly-Gly-Ser-Gly-Gly-Gly-Gly-Ser (SEQ ID NO: 5)

B. Gly-Gly-Gly-Gly-Ser-Gly-Gly-Gly-Gly-Ser- Gly-Gly-Gly-Gly-Ser (SEQ ID NO: 6)

C. Gly-Gly-Gly-Gly-Ser-Gly-Gly-Gly-Gly-Ser-Gly-Gly-Gly-Gly-Ser-Gly-Gly-Gly-Gly-Ser (SEQ ID NO: 7)

A = donor excitation peak

B = donor emission

C = acceptor excitation

D = acceptor emission

SEQUENCE LISTING

```
<160> NUMBER OF SEQ ID NOS: 72

<210> SEQ ID NO 1
<211> LENGTH: 720
<212> TYPE: DNA
<213> ORGANISM: Renilla reniformis

<400> SEQUENCE: 1

atggtgagta aacaaatatt gaagaacact ggattgcagg agatcatgtc gtttaaagtg      60

aatctggaag gtgtagtaaa caatcatgtg ttcacaatgg aaggttgtgg aaaaggaaat     120

attttattcg gaaaccaact ggttcagatt cgtgtcacaa aaggggtccc gcttccattt     180

gcatttgata ttctctcacc agctttccaa tacggcaacc gtacattcac gaaataccg     240

gaggatatat cagacttttt tatacaatca tttccagcgg gatttgtata cgaaagaacg     300

ttgcgttacg aagatggtgg actggttgaa atccgttcag atataaattt aatcgaggag     360

atgtttgtct acagagtgga atataaaggt agtaacttcc cgaatgatgg tccagtgatg     420

aagaagacaa tcacaggatt acaaccttcg ttcgaagttg tgtatatgaa cgatggcgtc     480

ttggttggcc aagtcattct tgtttataga ttaaactctg gcaaatttta ttcgtgtcac     540

atgagaacac tgatgaaatc aaagggtgta gtgaaggatt ttcccgaata ccatttcatt     600
```

-continued

```
caacatcgtt tagagaagac tgatgtggaa gacggaggtt ttgttgagca acacgagacg    660

gccattgctc aactgacatc gctggggaaa ccacttggat ccttacacga atgggtttaa    720
```

<210> SEQ ID NO 2
<211> LENGTH: 238
<212> TYPE: PRT
<213> ORGANISM: Renilla reniformis

<400> SEQUENCE: 2

```
Met Ser Lys Gln Ile Leu Lys Asn Thr Gly Leu Gln Glu Ile Met Ser
1               5                   10                  15

Phe Lys Val Asn Leu Glu Gly Val Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Val Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Glu Met Phe Val Tyr Arg Val Glu Tyr Lys
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Asp Val
        195                 200                 205

Glu Asp Gly Gly Phe Val Glu Gln His Glu Thr Ala Ile Ala Gln Leu
    210                 215                 220

Thr Ser Leu Gly Lys Pro Leu Gly Ser Leu His Glu Trp Val
225                 230                 235
```

<210> SEQ ID NO 3
<211> LENGTH: 720
<212> TYPE: DNA
<213> ORGANISM: Artificial sequence
<220> FEATURE:
<223> OTHER INFORMATION: R. reniformis GFP polynucleotide sequence adapted to humanize cod
      on usage

<400> SEQUENCE: 3

```
atggtgagca agcagatcct gaagaacacc tgcctgcagg aggtgatgag ctacaaggtg     60

aacctggagg gcatcgtgaa caaccacgtg ttcaccatgg agggctgcgg caagggcaac    120

atcctgttcg gcaaccagct ggtgcagatc cgcgtgacca agggcgcccc cctgcccttc    180

gccttcgaca tcgtgagccc cgccttccag tacggcaacc gcaccttcac caagtacccc    240

aacgacatca gcgactactt catccagagc ttccccgccg gcttcatgta cgagcgcacc    300

ctgcgctacg aggacggcgg cctggtggag atccgcagcg acatcaacct gatcgaggac    360
```

-continued

```
aagttcgtgt accgcgtgga gtacaagggc agcaacttcc ccgacgacgg ccccgtgatg    420

cagaagacca tcctgggcat cgagcccagc ttcgaggcca tgtacatgaa caacggcgtg    480

ctggtgggcg aggtgatcct ggtgtacaag ctgaacagcg gcaagtacta cagctgccac    540

atgaagaccc tgatgaagag caagggcgtg gtgaaggagt tcccctccta ccacttcatc    600

cagcaccgcc tggagaagac ctacgtggag gacggcggct tcgtggagca gcacgagacc    660

gccatcgccc agatgaccag catcggcaag cccctgggca gcctgcacga gtgggtgtaa    720
```

```
<210> SEQ ID NO 4
<211> LENGTH: 239
<212> TYPE: PRT
<213> ORGANISM: Artificial sequence
<220> FEATURE:
<223> OTHER INFORMATION: Sequence of R. reniformis GFP polypeptide encoded by humanized R.
      reniformis GFP polynucleotide sequence

<400> SEQUENCE: 4

Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Thr Glu Arg Thr Leu Arg Tyr Glu Asp Gly Gly Leu Val Glu Ile Arg
            100                 105                 110

Ser Asp Ile Asn Leu Ile Glu Glu Met Phe Val Tyr Arg Val Glu Tyr
        115                 120                 125

Lys Gly Ser Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235
```

```
<210> SEQ ID NO 5
<211> LENGTH: 10
<212> TYPE: PRT
<213> ORGANISM: Artificial sequence
<220> FEATURE:
<223> OTHER INFORMATION: Synthetic peptide linker sequnce

<400> SEQUENCE: 5
```

-continued

```
Gly Gly Gly Gly Ser Gly Gly Gly Gly Ser
1               5                   10


<210> SEQ ID NO 6
<211> LENGTH: 15
<212> TYPE: PRT
<213> ORGANISM: Artificial sequence
<220> FEATURE:
<223> OTHER INFORMATION: Synthetic linker peptide

<400> SEQUENCE: 6

Gly Gly Gly Gly Ser Gly Gly Gly Gly Ser Gly Gly Gly Gly Ser
1               5                   10                  15


<210> SEQ ID NO 7
<211> LENGTH: 20
<212> TYPE: PRT
<213> ORGANISM: Artificial sequence
<220> FEATURE:
<223> OTHER INFORMATION: Synthetic linker peptide

<400> SEQUENCE: 7

Gly Gly Gly Gly Ser Gly Gly Gly Gly Ser Gly Gly Gly Gly Ser Gly
1               5                   10                  15

Gly Gly Gly Ser
            20


<210> SEQ ID NO 8
<211> LENGTH: 11
<212> TYPE: PRT
<213> ORGANISM: Artificial sequence
<220> FEATURE:
<223> OTHER INFORMATION: Synthetic linker peptide

<400> SEQUENCE: 8

Arg Ala Arg Asp Pro Arg Val Pro Val Ala Thr
1               5                   10


<210> SEQ ID NO 9
<211> LENGTH: 2
<212> TYPE: PRT
<213> ORGANISM: Artificial Sequence
<220> FEATURE:
<223> OTHER INFORMATION: synthetic linker peptide

<400> SEQUENCE: 9

Gly Ser
1


<210> SEQ ID NO 10
<211> LENGTH: 4
<212> TYPE: PRT
<213> ORGANISM: Artificial Sequence
<220> FEATURE:
<223> OTHER INFORMATION: Synthetic linker peptide

<400> SEQUENCE: 10

Gly Ser Gly Ser
1


<210> SEQ ID NO 11
<211> LENGTH: 6
<212> TYPE: PRT
<213> ORGANISM: Artificial Sequence
<220> FEATURE:
<223> OTHER INFORMATION: Synthetic linker peptide
```

-continued

<400> SEQUENCE: 11

Gly Ser Gly Ser Gly Ser
1 5

<210> SEQ ID NO 12
<211> LENGTH: 8
<212> TYPE: PRT
<213> ORGANISM: Artificial Sequence
<220> FEATURE:
<223> OTHER INFORMATION: Synthetic linker peptide

<400> SEQUENCE: 12

Gly Ser Gly Ser Gly Ser Gly Ser
1 5

<210> SEQ ID NO 13
<211> LENGTH: 10
<212> TYPE: PRT
<213> ORGANISM: Artificial Sequence
<220> FEATURE:
<223> OTHER INFORMATION: Synthetic linker peptide

<400> SEQUENCE: 13

Gly Ser Gly Ser Gly Ser Gly Ser Gly Ser
1 5 10

<210> SEQ ID NO 14
<211> LENGTH: 12
<212> TYPE: PRT
<213> ORGANISM: Artificial Sequence
<220> FEATURE:
<223> OTHER INFORMATION: Synthetic linker peptide

<400> SEQUENCE: 14

Gly Ser Gly Ser Gly Ser Gly Ser Gly Ser Gly Ser
1 5 10

<210> SEQ ID NO 15
<211> LENGTH: 14
<212> TYPE: PRT
<213> ORGANISM: Artificial Sequence
<220> FEATURE:
<223> OTHER INFORMATION: Synthetic linker peptide

<400> SEQUENCE: 15

Gly Ser Gly Ser Gly Ser Gly Ser Gly Ser Gly Ser Gly Ser
1 5 10

<210> SEQ ID NO 16
<211> LENGTH: 16
<212> TYPE: PRT
<213> ORGANISM: Artificial Sequence
<220> FEATURE:
<223> OTHER INFORMATION: Synthetic linker peptide

<400> SEQUENCE: 16

Gly Ser Gly Ser Gly Ser Gly Ser Gly Ser Gly Ser Gly Ser Gly Ser
1 5 10 15

<210> SEQ ID NO 17
<211> LENGTH: 18
<212> TYPE: PRT
<213> ORGANISM: Artificial Sequence
<220> FEATURE:
<223> OTHER INFORMATION: Synthetic linker peptide

<400> SEQUENCE: 17

-continued

```
Gly Ser Gly Ser Gly Ser Gly Ser Gly Ser Gly Ser Gly Ser Gly Ser
1               5                   10                  15

Gly Ser


<210> SEQ ID NO 18
<211> LENGTH: 20
<212> TYPE: PRT
<213> ORGANISM: Artificial Sequence
<220> FEATURE:
<223> OTHER INFORMATION: Synthetic linker peptide

<400> SEQUENCE: 18

Gly Ser Gly Ser Gly Ser Gly Ser Gly Ser Gly Ser Gly Ser Gly Ser
1               5                   10                  15

Gly Ser Gly Ser
            20


<210> SEQ ID NO 19
<211> LENGTH: 22
<212> TYPE: PRT
<213> ORGANISM: Artificial Sequence
<220> FEATURE:
<223> OTHER INFORMATION: Synthetic linker peptide

<400> SEQUENCE: 19

Gly Ser Gly Ser Gly Ser Gly Ser Gly Ser Gly Ser Gly Ser Gly Ser
1               5                   10                  15

Gly Ser Gly Ser Gly Ser
            20


<210> SEQ ID NO 20
<211> LENGTH: 24
<212> TYPE: PRT
<213> ORGANISM: Artificial Sequence
<220> FEATURE:
<223> OTHER INFORMATION: Synthetic linker peptide

<400> SEQUENCE: 20

Gly Ser Gly Ser Gly Ser Gly Ser Gly Ser Gly Ser Gly Ser Gly Ser
1               5                   10                  15

Gly Ser Gly Ser Gly Ser Gly Ser
            20


<210> SEQ ID NO 21
<211> LENGTH: 26
<212> TYPE: PRT
<213> ORGANISM: Artificial Sequence
<220> FEATURE:
<223> OTHER INFORMATION: Synthetic linker peptide

<400> SEQUENCE: 21

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser
            20                  25


<210> SEQ ID NO 22
<211> LENGTH: 28
<212> TYPE: PRT
<213> ORGANISM: Artificial sequence
<220> FEATURE:
<223> OTHER INFORMATION: Synthetic linker peptide

<400> SEQUENCE: 22
```

-continued

```
Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser
            20                  25


<210> SEQ ID NO 23
<211> LENGTH: 30
<212> TYPE: PRT
<213> ORGANISM: Artificial Sequence
<220> FEATURE:
<223> OTHER INFORMATION: Synthetic linker peptide

<400> SEQUENCE: 23

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser
            20                  25                  30


<210> SEQ ID NO 24
<211> LENGTH: 3
<212> TYPE: PRT
<213> ORGANISM: Artificial sequence
<220> FEATURE:
<223> OTHER INFORMATION: Synthetic linker peptide

<400> SEQUENCE: 24

Thr Ser Pro
1


<210> SEQ ID NO 25
<211> LENGTH: 6
<212> TYPE: PRT
<213> ORGANISM: Artificial Sequence
<220> FEATURE:
<223> OTHER INFORMATION: Synthetic linker peptide

<400> SEQUENCE: 25

Thr Ser Pro Thr Ser Pro
1               5


<210> SEQ ID NO 26
<211> LENGTH: 9
<212> TYPE: PRT
<213> ORGANISM: Artificial Sequence
<220> FEATURE:
<223> OTHER INFORMATION: Synthetic linker peptide

<400> SEQUENCE: 26

Thr Ser Pro Thr Ser Pro Thr Ser Pro
1               5


<210> SEQ ID NO 27
<211> LENGTH: 12
<212> TYPE: PRT
<213> ORGANISM: Artificial Sequence
<220> FEATURE:
<223> OTHER INFORMATION: Synthetic linker peptide

<400> SEQUENCE: 27

Thr Ser Pro Thr Ser Pro Thr Ser Pro Thr Ser Pro
1               5                   10


<210> SEQ ID NO 28
<211> LENGTH: 15
<212> TYPE: PRT
```

-continued

<213> ORGANISM: Artificial Sequence
<220> FEATURE:
<223> OTHER INFORMATION: Synthetic linker peptide

<400> SEQUENCE: 28

```
Thr Ser Pro Thr Ser Pro Thr Ser Pro Thr Ser Pro Thr Ser Pro
1               5                   10                  15
```

<210> SEQ ID NO 29
<211> LENGTH: 18
<212> TYPE: PRT
<213> ORGANISM: Artificial Sequence
<220> FEATURE:
<223> OTHER INFORMATION: Synthetic linker peptide

<400> SEQUENCE: 29

```
Thr Ser Pro Thr Ser Pro Thr Ser Pro Thr Ser Pro Thr Ser Pro Thr
1               5                   10                  15

Ser Pro
```

<210> SEQ ID NO 30
<211> LENGTH: 21
<212> TYPE: PRT
<213> ORGANISM: Artificial Sequence
<220> FEATURE:
<223> OTHER INFORMATION: Synthetic linker peptide

<400> SEQUENCE: 30

```
Thr Ser Pro Thr Ser Pro Thr Ser Pro Thr Ser Pro Thr Ser Pro Thr
1               5                   10                  15

Ser Pro Thr Ser Pro
            20
```

<210> SEQ ID NO 31
<211> LENGTH: 24
<212> TYPE: PRT
<213> ORGANISM: Artificial Sequence
<220> FEATURE:
<223> OTHER INFORMATION: Synthetic linker peptide

<400> SEQUENCE: 31

```
Thr Ser Pro Thr Ser Pro Thr Ser Pro Thr Ser Pro Thr Ser Pro Thr
1               5                   10                  15

Ser Pro Thr Ser Pro Thr Ser Pro
            20
```

<210> SEQ ID NO 32
<211> LENGTH: 27
<212> TYPE: PRT
<213> ORGANISM: Artificial Sequence
<220> FEATURE:
<223> OTHER INFORMATION: Synthetic linker peptide

<400> SEQUENCE: 32

```
Thr Ser Pro Thr Ser Pro Thr Ser Pro Thr Ser Pro Thr Ser Pro Thr
1               5                   10                  15

Ser Pro Thr Ser Pro Thr Ser Pro Thr Ser Pro
            20                  25
```

<210> SEQ ID NO 33
<211> LENGTH: 30
<212> TYPE: PRT
<213> ORGANISM: Artificial Sequence
<220> FEATURE:
<223> OTHER INFORMATION: Synthetic linker peptide -continued

<400> SEQUENCE: 33

Thr Ser Pro Thr Ser Pro Thr Ser Pro Thr Ser Pro Thr Ser Pro Thr
1 5 10 15

Ser Pro Thr Ser Pro Thr Ser Pro Thr Ser Pro Thr Ser Pro
20 25 30

<210> SEQ ID NO 34
<211> LENGTH: 33
<212> TYPE: PRT
<213> ORGANISM: Artificial Sequence
<220> FEATURE:
<223> OTHER INFORMATION: Synthetic linker peptide

<400> SEQUENCE: 34

Thr Ser Pro Thr Ser Pro Thr Ser Pro Thr Ser Pro Thr Ser Pro Thr
1 5 10 15

Ser Pro Thr Ser Pro Thr Ser Pro Thr Ser Pro Thr Ser Pro Thr Ser
20 25 30

Pro

<210> SEQ ID NO 35
<211> LENGTH: 36
<212> TYPE: PRT
<213> ORGANISM: Artificial Sequence
<220> FEATURE:
<223> OTHER INFORMATION: Synthetic linker peptide

<400> SEQUENCE: 35

Thr Ser Pro Thr Ser Pro Thr Ser Pro Thr Ser Pro Thr Ser Pro Thr
1 5 10 15

Ser Pro Thr Ser Pro Thr Ser Pro Thr Ser Pro Thr Ser Pro Thr Ser
20 25 30

Pro Thr Ser Pro
35

<210> SEQ ID NO 36
<211> LENGTH: 39
<212> TYPE: PRT
<213> ORGANISM: Artificial Sequence
<220> FEATURE:
<223> OTHER INFORMATION: Synthetic linker peptide

<400> SEQUENCE: 36

Thr Ser Pro Thr Ser Pro Thr Ser Pro Thr Ser Pro Thr Ser Pro Thr
1 5 10 15

Ser Pro Thr Ser Pro Thr Ser Pro Thr Ser Pro Thr Ser Pro Thr Ser
20 25 30

Pro Thr Ser Pro Thr Ser Pro
35

<210> SEQ ID NO 37
<211> LENGTH: 42
<212> TYPE: PRT
<213> ORGANISM: Artificial Sequence
<220> FEATURE:
<223> OTHER INFORMATION: Synthetic linker peptide

<400> SEQUENCE: 37

Thr Ser Pro Thr Ser Pro Thr Ser Pro Thr Ser Pro Thr Ser Pro Thr
1 5 10 15

Ser Pro Thr Ser Pro Thr Ser Pro Thr Ser Pro Thr Ser Pro Thr Ser

-continued

```
            20                  25                  30

Pro Thr Ser Pro Thr Ser Pro Thr Ser Pro
        35                  40


<210> SEQ ID NO 38
<211> LENGTH: 45
<212> TYPE: PRT
<213> ORGANISM: Artificial Sequence
<220> FEATURE:
<223> OTHER INFORMATION: Synthetic linker peptide

<400> SEQUENCE: 38

Thr Ser Pro Thr Ser Pro Thr Ser Pro Thr Ser Pro Thr Ser Pro Thr
1               5                   10                  15

Ser Pro Thr Ser Pro Thr Ser Pro Thr Ser Pro Thr Ser Pro Thr Ser
            20                  25                  30

Pro Thr Ser Pro Thr Ser Pro Thr Ser Pro Thr Ser Pro
        35                  40                  45


<210> SEQ ID NO 39
<211> LENGTH: 3
<212> TYPE: PRT
<213> ORGANISM: Artificial Sequence
<220> FEATURE:
<223> OTHER INFORMATION: Synthetic linker peptide

<400> SEQUENCE: 39

Gly Gly Gly
1


<210> SEQ ID NO 40
<211> LENGTH: 6
<212> TYPE: PRT
<213> ORGANISM: Artificial Sequence
<220> FEATURE:
<223> OTHER INFORMATION: Synthetic linker peptide

<400> SEQUENCE: 40

Gly Gly Gly Gly Gly Gly
1               5


<210> SEQ ID NO 41
<211> LENGTH: 9
<212> TYPE: PRT
<213> ORGANISM: Artificial Sequence
<220> FEATURE:
<223> OTHER INFORMATION: Synthetic linker peptide

<400> SEQUENCE: 41

Gly Gly Gly Gly Gly Gly Gly Gly Gly
1               5


<210> SEQ ID NO 42
<211> LENGTH: 12
<212> TYPE: PRT
<213> ORGANISM: Artificial Sequence
<220> FEATURE:
<223> OTHER INFORMATION: Synthetic linker peptide

<400> SEQUENCE: 42

Gly Gly Gly Gly Gly Gly Gly Gly Gly Gly Gly Gly
1               5                   10


<210> SEQ ID NO 43
<211> LENGTH: 15
```

-continued

<212> TYPE: PRT
<213> ORGANISM: Artificial Sequence
<220> FEATURE:
<223> OTHER INFORMATION: Synthetic linker peptide

<400> SEQUENCE: 43

Gly Gly Gly Gly Gly Gly Gly Gly Gly Gly Gly Gly Gly Gly Gly
1 5 10 15

<210> SEQ ID NO 44
<211> LENGTH: 18
<212> TYPE: PRT
<213> ORGANISM: Artificial Sequence
<220> FEATURE:
<223> OTHER INFORMATION: Synthetic linker peptide

<400> SEQUENCE: 44

Gly Gly Gly Gly Gly Gly Gly Gly Gly Gly Gly Gly Gly Gly Gly Gly
1 5 10 15

Gly Gly

<210> SEQ ID NO 45
<211> LENGTH: 21
<212> TYPE: PRT
<213> ORGANISM: Artificial Sequence
<220> FEATURE:
<223> OTHER INFORMATION: Synthetic linker peptide

<400> SEQUENCE: 45

Gly Gly Gly Gly Gly Gly Gly Gly Gly Gly Gly Gly Gly Gly Gly Gly
1 5 10 15

Gly Gly Gly Gly Gly
20

<210> SEQ ID NO 46
<211> LENGTH: 24
<212> TYPE: PRT
<213> ORGANISM: Artificial Sequence
<220> FEATURE:
<223> OTHER INFORMATION: Synthetic linker peptide

<400> SEQUENCE: 46

Gly Gly Gly Gly Gly Gly Gly Gly Gly Gly Gly Gly Gly Gly Gly Gly
1 5 10 15

Gly Gly Gly Gly Gly Gly Gly Gly
20

<210> SEQ ID NO 47
<211> LENGTH: 27
<212> TYPE: PRT
<213> ORGANISM: Artificial Sequence
<220> FEATURE:
<223> OTHER INFORMATION: Synthetic linker peptide

<400> SEQUENCE: 47

Gly Gly Gly Gly Gly Gly Gly Gly Gly Gly Gly Gly Gly Gly Gly Gly
1 5 10 15

Gly Gly Gly Gly Gly Gly Gly Gly Gly Gly Gly
20 25

<210> SEQ ID NO 48
<211> LENGTH: 30
<212> TYPE: PRT
<213> ORGANISM: Artificial Sequence
<220> FEATURE:

-continued

<223> OTHER INFORMATION: Synthetic linker peptide

<400> SEQUENCE: 48

Gly Gly Gly Gly Gly Gly Gly Gly Gly Gly Gly Gly Gly Gly Gly Gly
1 5 10 15

Gly Gly Gly Gly Gly Gly Gly Gly Gly Gly Gly Gly Gly Gly
20 25 30

<210> SEQ ID NO 49
<211> LENGTH: 33
<212> TYPE: PRT
<213> ORGANISM: Artificial Sequence
<220> FEATURE:
<223> OTHER INFORMATION: Synthetic linker peptide

<400> SEQUENCE: 49

Gly Gly Gly Gly Gly Gly Gly Gly Gly Gly Gly Gly Gly Gly Gly Gly
1 5 10 15

Gly Gly Gly Gly Gly Gly Gly Gly Gly Gly Gly Gly Gly Gly Gly Gly
20 25 30

Gly

<210> SEQ ID NO 50
<211> LENGTH: 36
<212> TYPE: PRT
<213> ORGANISM: Artificial Sequence
<220> FEATURE:
<223> OTHER INFORMATION: Synthetic linker peptide

<400> SEQUENCE: 50

Gly Gly Gly Gly Gly Gly Gly Gly Gly Gly Gly Gly Gly Gly Gly Gly
1 5 10 15

Gly Gly Gly Gly Gly Gly Gly Gly Gly Gly Gly Gly Gly Gly Gly Gly
20 25 30

Gly Gly Gly Gly
35

<210> SEQ ID NO 51
<211> LENGTH: 39
<212> TYPE: PRT
<213> ORGANISM: Artificial Sequence
<220> FEATURE:
<223> OTHER INFORMATION: Synthetic linker peptide

<400> SEQUENCE: 51

Gly Gly Gly Gly Gly Gly Gly Gly Gly Gly Gly Gly Gly Gly Gly Gly
1 5 10 15

Gly Gly Gly Gly Gly Gly Gly Gly Gly Gly Gly Gly Gly Gly Gly Gly
20 25 30

Gly Gly Gly Gly Gly Gly Gly
35

<210> SEQ ID NO 52
<211> LENGTH: 42
<212> TYPE: PRT
<213> ORGANISM: Artificial Sequence
<220> FEATURE:
<223> OTHER INFORMATION: Synthetic linker peptide

<400> SEQUENCE: 52

Gly Gly Gly Gly Gly Gly Gly Gly Gly Gly Gly Gly Gly Gly Gly Gly
1 5 10 15

-continued

```
Gly Gly Gly Gly Gly Gly Gly Gly Gly Gly Gly Gly Gly Gly Gly Gly
            20                  25                  30

Gly Gly Gly Gly Gly Gly Gly Gly Gly Gly
        35                  40


<210> SEQ ID NO 53
<211> LENGTH: 45
<212> TYPE: PRT
<213> ORGANISM: Artificial Sequence
<220> FEATURE:
<223> OTHER INFORMATION: Synthetic linker peptide

<400> SEQUENCE: 53

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly
        35                  40                  45


<210> SEQ ID NO 54
<211> LENGTH: 2
<212> TYPE: PRT
<213> ORGANISM: Artificial Sequence
<220> FEATURE:
<223> OTHER INFORMATION: Synthetic linker peptide

<400> SEQUENCE: 54

Glu Lys
1


<210> SEQ ID NO 55
<211> LENGTH: 4
<212> TYPE: PRT
<213> ORGANISM: Artificial Sequence
<220> FEATURE:
<223> OTHER INFORMATION: Synthetic linker peptide

<400> SEQUENCE: 55

Glu Lys Glu Lys
1


<210> SEQ ID NO 56
<211> LENGTH: 6
<212> TYPE: PRT
<213> ORGANISM: Artificial Sequence
<220> FEATURE:
<223> OTHER INFORMATION: Synthetic linker peptide

<400> SEQUENCE: 56

Glu Lys Glu Lys Glu Lys
1               5


<210> SEQ ID NO 57
<211> LENGTH: 8
<212> TYPE: PRT
<213> ORGANISM: Artificial Sequence
<220> FEATURE:
<223> OTHER INFORMATION: Synthetic linker peptide

<400> SEQUENCE: 57

Glu Lys Glu Lys Glu Lys Glu Lys
1               5


<210> SEQ ID NO 58
```

-continued

<211> LENGTH: 10
<212> TYPE: PRT
<213> ORGANISM: Artificial Sequence
<220> FEATURE:
<223> OTHER INFORMATION: Synthetic linker peptide

<400> SEQUENCE: 58

Glu Lys Glu Lys Glu Lys Glu Lys Glu Lys
1 5 10

<210> SEQ ID NO 59
<211> LENGTH: 12
<212> TYPE: PRT
<213> ORGANISM: Artificial Sequence
<220> FEATURE:
<223> OTHER INFORMATION: Synthetic linker peptide

<400> SEQUENCE: 59

Glu Lys Glu Lys Glu Lys Glu Lys Glu Lys Glu Lys
1 5 10

<210> SEQ ID NO 60
<211> LENGTH: 14
<212> TYPE: PRT
<213> ORGANISM: Artificial Sequence
<220> FEATURE:
<223> OTHER INFORMATION: Synthetic linker peptide

<400> SEQUENCE: 60

Glu Lys Glu Lys Glu Lys Glu Lys Glu Lys Glu Lys Glu Lys
1 5 10

<210> SEQ ID NO 61
<211> LENGTH: 16
<212> TYPE: PRT
<213> ORGANISM: Artificial Sequence
<220> FEATURE:
<223> OTHER INFORMATION: Synthetic linker peptide

<400> SEQUENCE: 61

Glu Lys Glu Lys Glu Lys Glu Lys Glu Lys Glu Lys Glu Lys Glu Lys
1 5 10 15

<210> SEQ ID NO 62
<211> LENGTH: 18
<212> TYPE: PRT
<213> ORGANISM: Artificial Sequence
<220> FEATURE:
<223> OTHER INFORMATION: Synthetic linker peptide

<400> SEQUENCE: 62

Glu Lys Glu Lys Glu Lys Glu Lys Glu Lys Glu Lys Glu Lys Glu Lys
1 5 10 15

Glu Lys

<210> SEQ ID NO 63
<211> LENGTH: 20
<212> TYPE: PRT
<213> ORGANISM: Artificial Sequence
<220> FEATURE:
<223> OTHER INFORMATION: Synthetic linker peptide

<400> SEQUENCE: 63

Glu Lys Glu Lys Glu Lys Glu Lys Glu Lys Glu Lys Glu Lys Glu Lys
1 5 10 15

Glu Lys Glu Lys

-continued

20

<210> SEQ ID NO 64
<211> LENGTH: 22
<212> TYPE: PRT
<213> ORGANISM: Artificial Sequence
<220> FEATURE:
<223> OTHER INFORMATION: Synthetic linker peptide

<400> SEQUENCE: 64

```
Glu Lys Glu Lys Glu Lys Glu Lys Glu Lys Glu Lys Glu Lys Glu Lys
1               5                   10                  15

Glu Lys Glu Lys Glu Lys
            20
```

<210> SEQ ID NO 65
<211> LENGTH: 24
<212> TYPE: PRT
<213> ORGANISM: Artificial Sequence
<220> FEATURE:
<223> OTHER INFORMATION: Synthetic linker peptide

<400> SEQUENCE: 65

```
Glu Lys Glu Lys Glu Lys Glu Lys Glu Lys Glu Lys Glu Lys Glu Lys
1               5                   10                  15

Glu Lys Glu Lys Glu Lys Glu Lys
            20
```

<210> SEQ ID NO 66
<211> LENGTH: 26
<212> TYPE: PRT
<213> ORGANISM: Artificial Sequence
<220> FEATURE:
<223> OTHER INFORMATION: Synthetic linker peptide

<400> SEQUENCE: 66

```
Glu Lys Glu Lys Glu Lys Glu Lys Glu Lys Glu Lys Glu Lys Glu Lys
1               5                   10                  15

Glu Lys Glu Lys Glu Lys Glu Lys Glu Lys
            20                  25
```

<210> SEQ ID NO 67
<211> LENGTH: 28
<212> TYPE: PRT
<213> ORGANISM: Artificial Sequence
<220> FEATURE:
<223> OTHER INFORMATION: Synthetic linker peptide

<400> SEQUENCE: 67

```
Glu Lys Glu Lys Glu Lys Glu Lys Glu Lys Glu Lys Glu Lys Glu Lys
1               5                   10                  15

Glu Lys Glu Lys Glu Lys Glu Lys Glu Lys Glu Lys
            20                  25
```

<210> SEQ ID NO 68
<211> LENGTH: 30
<212> TYPE: PRT
<213> ORGANISM: Artificial Sequence
<220> FEATURE:
<223> OTHER INFORMATION: Synthetic linker peptide

<400> SEQUENCE: 68

```
Glu Lys Glu Lys Glu Lys Glu Lys Glu Lys Glu Lys Glu Lys Glu Lys
1               5                   10                  15
```

-continued

```
Glu Lys Glu Lys Glu Lys Glu Lys Glu Lys Glu Lys Glu Lys
            20                  25                  30


<210> SEQ ID NO 69
<211> LENGTH: 22
<212> TYPE: PRT
<213> ORGANISM: Artificial Sequence
<220> FEATURE:
<223> OTHER INFORMATION: Synthetic linker peptide

<400> SEQUENCE: 69

Arg Ala Arg Asp Pro Arg Val Pro Val Ala Thr Arg Ala Arg Asp Pro
1               5                   10                  15

Arg Val Pro Val Ala Thr
            20


<210> SEQ ID NO 70
<211> LENGTH: 33
<212> TYPE: PRT
<213> ORGANISM: Artificial Sequence
<220> FEATURE:
<223> OTHER INFORMATION: Synthetic linker peptide

<400> SEQUENCE: 70

Arg Ala Arg Asp Pro Arg Val Pro Val Ala Thr Arg Ala Arg Asp Pro
1               5                   10                  15

Arg Val Pro Val Ala Thr Arg Ala Arg Asp Pro Arg Val Pro Val Ala
            20                  25                  30

Thr


<210> SEQ ID NO 71
<211> LENGTH: 44
<212> TYPE: PRT
<213> ORGANISM: Artificial Sequence
<220> FEATURE:
<223> OTHER INFORMATION: Synthetic linker peptide

<400> SEQUENCE: 71

Arg Ala Arg Asp Pro Arg Val Pro Val Ala Thr Arg Ala Arg Asp Pro
1               5                   10                  15

Arg Val Pro Val Ala Thr Arg Ala Arg Asp Pro Arg Val Pro Val Ala
            20                  25                  30

Thr Arg Ala Arg Asp Pro Arg Val Pro Val Ala Thr
        35                  40


<210> SEQ ID NO 72
<211> LENGTH: 55
<212> TYPE: PRT
<213> ORGANISM: Artificial Sequence
<220> FEATURE:
<223> OTHER INFORMATION: Synthetic linker peptide

<400> SEQUENCE: 72

Arg Ala Arg Asp Pro Arg Val Pro Val Ala Thr Arg Ala Arg Asp Pro
1               5                   10                  15

Arg Val Pro Val Ala Thr Arg Ala Arg Asp Pro Arg Val Pro Val Ala
            20                  25                  30

Thr Arg Ala Arg Asp Pro Arg Val Pro Val Ala Thr Arg Ala Arg Asp
        35                  40                  45

Pro Arg Val Pro Val Ala Thr
    50                  55
```

DIMERIC FLOURESCENT POLYPEPTIDES

This application is a non-provisional application which claims priority under 35 U.S.C. §119(e) to U.S. Provisional Application Ser. No. 60/256,121 filed Dec. 15, 2000, the entirety of which is incorporated herein by reference.

BACKGROUND OF THE INVENTION

Fluorescent proteins are widely used in the fields of biochemistry, molecular and cell biology, medical diagnostics and drug screening methodologies (Chalfie et al., 1994, Science 263: 802–805; Tsien, 1998, Ann. Rev. Biochem. 67: 509–544). One property shared by the most useful fluorescent proteins is that they require no host-encoded co-factors or substrates for fluorescence. The proteins therefore retain their fluorescent properties both in isolation from their native organism, and when expressed in the cells of other organisms. This property makes them particularly well suited for a variety of in vivo and in vitro applications. Another major advantage of fluorescent proteins for use in biological systems is that they are indeed proteins, which permits their synthesis, within cells or organisms of interest, avoiding a host of problems relating to the attachment of the label to a protein of interest and/or delivery of labeled proteins into a cell. Not only can the proteins be made within the desired cell or organism, but they also retain their fluorescent properties when expressed as fusions with other proteins of interest, which greatly enhances their utility both in vivo and in vitro.

Fluorescent proteins have been used as reporter molecules to study gene expression in culture as well as in transgenic animals by insertion of fluorescent protein coding sequences downstream of an appropriate promoter. They have also been used to study the subcellular localization of proteins by direct fusion of test proteins to fluorescent proteins, and fluorescent proteins have become the reporter of choice for monitoring the infection efficiency of viral vectors both in cell culture and in animals. Variants of fluorescent proteins exhibiting spectral shifts in response to changes in the cellular environment (e.g., changes in pH, ion flux, or the redox status of the cell) are also used to monitor such changes (see, for example, Inouye & Tsuji, 1994, FEBS Lett. 351: 211–214; Miyawaki et al., 1997, Nature 388: 882–887).

Perhaps the most promising role for fluorescent proteins as biochemical markers is their application to methods that exploit fluorescence resonance energy transfer (FRET). FRET occurs with fluorophores for which the emission spectrum of one fluorophore overlaps with the excitation spectrum of a second fluorophore. When such fluorophores are brought into close proximity, excitation of the "donor" fluorophore results in emission from the "acceptor". Pairs of such fluorophores are thus useful for monitoring molecular interactions. Fluorescent proteins are useful for the analysis of protein:protein molecular interactions in vivo or in vitro if their respective fluorescent emission and excitation spectra overlap to allow FRET. The donor and acceptor fluorescent proteins may be produced as fusions with the proteins one wishes to analyze for interactions. These types of applications of fluorescent proteins are particularly appealing for high throughput analyses, since the readout is direct and independent of subcellular localization.

The prototypical fluorescent protein is the *Aequorea victoria* green fluorescent protein (GFP), which was the first green fluorescent protein cloned (Prasher et al., 1992, Gene 111: 229–233). Purified *A. victoria* GFP is a monomeric protein of about 27 kDa that absorbs blue light with an excitation wavelength maximum of 395 nm, with a minor peak at 470 nm, and emits green fluorescence with an emission wavelength of about 510 nm and a minor peak near 540 nm (Ward et al., 1979, Photochem. Photobiol. Rev. 4: 1–57). The polypeptide has several drawbacks, including relatively broad excitation and emission spectra, low quantum yield, and low expression in cells of higher eukaryotes. Mutants with improved spectral characteristics and higher quantum yield have been identified, and expression in higher eukaryotes has been improved by "humanizing" the nucleic acid sequences to encode codons optimized for human or mammalian expression.

Additional fluorescent proteins include, but are not limited to those expressed by *Discosoma sp.* and *Phialidium gregarum* (Ward et al., 1982, Photochem. Photobiol. 35: 803–808; Levine et al., 1982, Comp. Biochem. Physiol. 72B:77–85). Also, *Vibrio fischeri* strain Y1 expresses a yellow fluorescent protein that requires flavins as a co-factor for its fluorescence (Baldwin et al., 1990, Biochemistry 29: 5509–5515).

Additional cloned fluorescent proteins include, for example, the green fluorescent proteins from the sea pansy, *Renilla mullerei* (WO/99/49019) and from *Renilla reniformis* (see SEQ ID NO: 1; FIG. 1). Each of these fluorescent proteins and others are useful for a variety of in vivo and in vitro uses. The *R. reniformis* GFP (rGFP) clone is particularly important, since rGFP is seen as the benchmark protein among known naturally-occurring fluorescent proteins. rGFP has 3 to 6-fold higher quantum yield than *A. victoria* GFP, and the excitation and emission spectra are narrower, making rGFP more suitable for applications involving, for example, FRET.

One major drawback shared by the GFPs from *A. victoria, R. mullerei* and *R. reniformis,* as well as by all known variants of those proteins, is that they are dimeric. Generally, the proteins exist as homodimers. However, when more than one form of a given GFP is expressed in a single cell or is mixed in vitro, heterodimers can form if the dimerization interfaces for the different fluorescent proteins are complementary. Heterodimerization interferes with the usefulness of fluorescent proteins for several reasons.

First, heterodimerization is undesirable when fluorescent proteins are used in energy transfer-based analyses because heterodimerization raises the background of acceptor fluorescence without a real interaction between the proteins or protein domains of interest. When FRET is used, for example to monitor protein:protein interactions, donor and acceptor fluorescent fusion proteins are often expressed in the same cell or otherwise mixed. In the absence of heterodimerization, the excitation of the donor fluorophore leads to emission by the acceptor fluorophore only if the two fusion proteins are in close apposition. However, if heterodimerization occurs between the differing fluorescent proteins (e.g., between a wild-type rGFP and an rGFP variant that is a fluorescence donor to the wild-type GFP), excitation of the donor will result in emission by the acceptor regardless of the interaction between the fused polypeptides being examined for interaction. This generates an unacceptably high background fluorescence from the acceptor fluorophore.

Another problem caused by the heterodimerization is that the dimerization interfaces between the proteins can serve to artifactually bring fusion polypeptides linked to the fluorescent protein monomers into close contact. The inappropriate recruitment of proteins into close apposition can have biological consequences that make data interpretation difficult.

For example, some cell surface receptors gain the ability to initiate an intracellular signaling cascade following ligand-induced dimerization. If the dimerization interfaces of the fluorescent proteins inappropriately recruit the fused receptor monomers into close contact, the signaling cascade can be inappropriately initiated in the absence of ligand. There is a need in the art for fluorescent proteins that do not heterodimerize.

U.S. Pat. No. 5,981,200 (Tsien et al.) teaches donor and acceptor fluorescent proteins linked by a peptide linker. The linked donor and acceptor proteins, referred to as "tandem fluorescent proteins," are taught to be useful for assaying enzymes capable of cleaving the linker peptide sequence. When linked, the tandem fluorescent proteins exhibit either no fluorescence (e.g., when one protein quenches the fluorescence of the other) or fluorescence characteristic of the acceptor. Following cleavage, the fluorescence emitted is that characteristic of the individual fluorescent proteins. Assays using this arrangement will not work unless the tandem fluorescent proteins are related as donor and acceptor.

SUMMARY OF THE INVENTION

The invention encompasses a recombinant fusion polypeptide comprising a first polypeptide peptide bonded to a second polypeptide, wherein the first and second polypeptides are found in nature as monomers of a multimeric protein, and wherein the recombinant fusion polypeptide is fluorescent when exposed to light of an excitation wavelength or when interactive with an excited donor fluorophore.

In one embodiment, the first polypeptide and the second polypeptide are peptide bonded to each other via a linker sequence.

In another embodiment, the recombinant fusion polypeptide further comprises a third polypeptide peptide bonded to the recombinant fusion polypeptide. The third polypeptide can be peptide bonded to the recombinant fusion polypeptide either directly or through a peptide linker sequence. A recombinant fusion polypeptide of this embodiment is referred to in this summary as a "fluorescent polypeptide fusion." In a preferred embodiment, the third polypeptide is fused to the amino terminus of the first polypeptide. In another preferred embodiment, the third polypeptide is fused to the carboxy terminus of the second polypeptide sequence.

In an additional preferred embodiment, the third polypeptide is a member of a specific binding pair.

In another embodiment, one or both of the first and second polypeptides is a monomer of one of *R. reniformis* GFP, *R. mulleri* GFP or *A. victoria* GFP.

In another embodiment, both of the first and second polypeptides are a monomer of one of *R. reniformis* GFP, *R. mulleri* GFP or *A. victoria* GFP.

The invention further encompasses a polynucleotide encoding, a recombinant fusion polypeptide comprising a first polypeptide peptide bonded to a second polypeptide, wherein the first and second polypeptides are found in nature as monomers of a multimeric protein, and wherein the recombinant fusion polypeptide is fluorescent when exposed to light of an excitation wavelength or when interactive with an excited donor fluorophore.

In one embodiment, the first polypeptide and the second polypeptide encoded by the polynucleotide are peptide bonded to each other via a linker sequence. In a preferred embodiment, the linker sequence encoded by the polynucleotide is from 5 to 50 amino acids long. In a further preferred embodiment, the linker sequence comprises one or more iterations of a peptide, for example the peptide RARDPRVP VAT (SEQ ID NO: 8; i.e., Arg-Ala-Arg-Asp-Pro-Arg-Val-Pro-Val-Ala-Thr). In a further preferred embodiment, the linker sequence is selected from the group consisting of $(\text{Arg-Ala-Arg-Asp-Pro-Arg-Val-Pro-Val-Ala-Thr})_n$ (SEQ ID NO: 8), $(\text{Gly-Ser})_n$, $(\text{Thr-Ser-Pro})_n$, $(\text{Gly-Gly-Gly})_n$, and $(\text{Glu-Lys})_n$, wherein n is 1 to 15.

In another embodiment, the polynucleotide further encodes a third polypeptide peptide bonded to the recombinant fusion polypeptide. The third polypeptide encoded by the polynucleotide may be joined directly or via an encoded peptide linker.

In a preferred embodiment, the third polypeptide encoded by the polynucleotide is a member of a specific binding pair. It alternatively preferred that the third encoded polypeptide is fused to the amino terminus of the first polypeptide. Is additionally preferred that the third encoded polypeptide is fused to the carboxy terminus of the second polypeptide.

In another preferred embodiment, one or both of the first and second polypeptides is a monomer of one of *R. reniformis* GFP, *R. mulleri* GFP, *A. victoria* GFP.

In another preferred embodiment, both of the first and second polypeptides is a monomer of one of *R. reniformis* GFP, *R. mulleri* GFP, *A. victoria* GFP.

The invention further encompasses a vector comprising a polynucleotide encoding a recombinant fusion polypeptide comprising a first polypeptide peptide bonded to a second polypeptide, wherein the first and second polypeptides are found in nature as monomers of a multimeric protein, and wherein the recombinant fusion polypeptide is fluorescent when exposed to light of an excitation wavelength or when interactive with an excited donor fluorophore.

The invention further encompasses a cell comprising a vector comprising a polynucleotide encoding a recombinant fusion polypeptide comprising a first polypeptide peptide bonded to a second polypeptide, wherein the first and second polypeptides are found in nature as monomers of a multimeric protein, and wherein the recombinant fusion polypeptide is fluorescent, when exposed to light of an excitation wavelength or when interactive with an excited donor fluorophore.

In one embodiment, the cell is a bacterial cell.

In another embodiment, the cell is a eukaryotic cell. In a preferred embodiment, the eukaryotic cell is a yeast cell, an insect cell, or a mammalian cell.

The invention further encompasses a pair of polypeptides comprising a polypeptide labeled with a fluorescent dye and a recombinant fusion polypeptide comprising a first polypeptide peptide bonded to a second polypeptide, wherein the first and second polypeptides are found in nature as monomers of a multimeric protein, wherein the fusion polypeptide is fluorescent when exposed to light of an excitation wavelength or when interactive with an excited donor fluorophore, and wherein the fluorescent dye and the recombinant fusion polypeptide are fluorescent donor and acceptor to each other.

The invention further encompasses a pair of recombinant fusion polypeptides comprising (a) a first fusion polypeptide comprising a first polypeptide peptide bonded to a second polypeptide, wherein the first and second polypeptides are found in nature as monomers of a multimeric protein, and wherein the first fusion polypeptide is fluorescent when exposed to light of an excitation wavelength or when interactive with an excited donor fluorophore, and (b) a second fusion polypeptide comprising a third polypeptide peptide bonded to a fourth polypeptide, wherein the third and fourth polypeptides are found in nature as monomers of a multimeric protein, and wherein the second fusion polypeptide is fluorescent when exposed to light of an excitation wavelength or when interactive with an excited donor fluorophore, wherein the first fusion polypeptide and the second fusion polypeptide are fluorescent donor and acceptor to each other.

In one embodiment, each of the first and second fusion polypeptides further comprises an additional fused (third) polypeptide, wherein the additional fused polypeptide of the first fusion polypeptide comprises a sequence which is different from the additional fused polypeptide of the second fusion polypeptide.

The invention further encompasses a method of producing a fluorescently labeled recombinant fusion polypeptide, the method comprising the, steps of introducing to a cell a polynucleotide encoding a recombinant fusion polypeptide comprising a first polypeptide peptide bonded to a second polypeptide, wherein the first and second polypeptides are found in nature as, monomers of a multimeric protein, and wherein the recombinant fusion polypeptide is fluorescent when exposed to light of an excitation wavelength or when interactive with an excited donor fluorophore, and culturing the cell under conditions that permit the synthesis of the recombinant fusion polypeptide, whereby the recombinant fusion polypeptide is produced.

The invention further encompasses a method of labeling a cell with a fluorescent recombinant fusion polypeptide, the method comprising the steps of: a) introducing to a cell a polynucleotide encoding a recombinant fusion polypeptide comprising a first polypeptide peptide bonded to a second polypeptide, wherein the first and second polypeptides are found in nature as monomers of a multimeric protein, and wherein the recombinant fusion polypeptide is fluorescent when exposed to light of an excitation wavelength or when interactive with an excited donor fluorophore; and b) culturing the cell under conditions that permit the synthesis of the recombinant fusion polypeptide, whereby the cell is labeled with the fluorescent recombinant fusion polypeptide.

In a preferred embodiment, in the introducing step (a), the polynucleotide introduced to the cell further comprises a sequence encoding a third polypeptide fused in frame to the sequence encoding the recombinant fusion polypeptide.

The invention further encompasses a method of monitoring the interaction of two polypeptides of interest, the method comprising the steps of: a) contacting a fluorescent polypeptide fusion, as described above, and a second polypeptide wherein: i) the fluorescent polypeptide fusion comprises a first polypeptide of interest; ii) the second polypeptide comprises a second polypeptide of interest and is fluorescently labeled;, and iii) the fluorophores comprised by the fluorescent polypeptide fusion and the second polypeptide are fluorescent donor and fluorescent acceptor to each other; b) exciting the donor fluorophore; and c) detecting fluorescent emission from the fluorescent acceptor, wherein the emission is indicative of the interaction of the first and the second polypeptides of interest.

In one embodiment, the second polypeptide comprises a second fluorescent polypeptide fusion, as described above, wherein the polypeptide of interest of the second fluorescent polypeptide fusion is different from the polypeptide of interest of the first fluorescent polypeptide fusion.

In one embodiment, the contacting step is performed in vitro.

In another embodiment, the contacting step is performed in a cell. In a preferred embodiment, the contacting comprises the step of introducing nucleic acid encoding the polypeptides to a cell.

The invention further encompasses a method of screening for a compound that modulates the interaction of a first and a second member of a specific binding pair, the method comprising the steps of: a) contacting a first polypeptide and a second polypeptide in the presence and absence of a candidate modulator wherein: i) the first polypeptide is a fluorescent polypeptide fusion, as described above, wherein the third polypeptide is the first member of a specific binding pair; ii) the second polypeptide is fluorescently labeled and comprises the second member of a specific binding pair; and iii) the fluorophores comprised by the first and second polypeptides are fluorescent donor and acceptor to each other; b) exciting the donor fluorophore; and c) detecting the fluorescence of the acceptor fluorophore, wherein emission of the spectrum characteristic of the fluorescent acceptor indicates the interaction of the first and the second members of the specific binding pair, and wherein a change in the interaction in the presence of the candidate modulator indicates that the candidate modulator modulates the interaction of the members of the specific binding pair.

In one embodiment, the second polypeptide is a fluorescent polypeptide fusion, as described above, which comprises the second member of a specific binding pair.

BRIEF DESCRIPTION OF THE FIGURES

FIG. 1 shows the polynucleotide sequence of *R. reniformis* GFP (SEQ ID NO: 1).

FIG. 2 shows the amino acid sequence of *R. reniformis* GFP (SEQ ID NO: 2).

FIG. 3 shows the polynucleotide and amino acid sequences for hrGFP, a humanized *R. reniformis* GFP. The polynucleotide sequence is SEQ ID NO: 3, and the amino acid sequence is SEQ ID NO: 4.

DETAILED DESCRIPTION OF THE INVENTION

Figure 4:
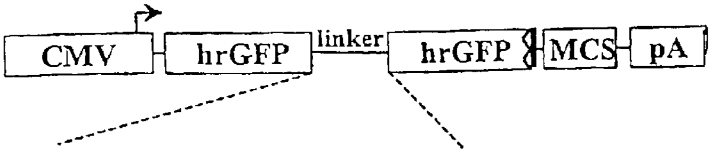
FIG. 4 shows a schematic diagram of a construct encoding an IDFP of the invention. "CMV" refers to the cytomegalovirus promoter, "MCS" refers to a multiple cloning sequence and "pA" refers to a poly(A) addition site sequence. "hrGFP" represents one monomer of the humanized *R. reniformis* GFP, and "linker" refers to a peptide or polypeptide linker sequence. A, B, and C show examples of linker peptide sequences.

All patents and patent applications, both U.S. and international, and all literature publications referred to herein are hereby incorporated in their entirety within this document by reference.

Definitions

As used herein, a recombinant fusion polypeptide is "fluorescent when excited".

As used herein, the term "excited" refers to a fluorophore that is exposed to light of an excitation wavelength or to an acceptor fluorophore that is interactive with an excited donor fluorophore.

The phrase "fluorescent when excited" means that when the recombinant fusion polypeptide is exposed to light of an excitation wavelength or when the polypeptide interacts with an excited donor fluorophore, the polypeptide fluoresces. "Exposed to light of an excitation wavelength" means irradiated with light (electromagnetic radiation) within a given spectrum of wavelengths that is absorbed by the polypeptide such that the polypeptide emits light having a different spectrum of wavelengths, and thus fluoresces. Fluorescent emission occurs at a longer wavelength than does excitation.

A recombinant fusion polypeptide according to the invention has three properties: 1) it must emit light upon irradiation with light of a given wavelength or wavelengths; 2) it must have the capacity to form an intramolecular homodimer as defined herein above; and 3) the first and second polypeptide monomers that constitute the fusion polypeptide cannot function as fluorescent donor and fluorescent acceptor, respectively, in the context of fluorescence resonance energy transfer.

As used herein, the term "light of an excitation wavelength" refers to those wavelengths of light that are absorbed by and excite a given fluorophore to emit fluorescence. These wavelengths are described in detail herein below. Light of an appropriate portion of the spectrum is synonymous with light within the excitation spectrum of a given fluorophore.

As used herein, the term "excited donor fluorophore" refers to a fluorophore which has absorbed energy within its excitation spectrum. An excited donor fluorophore can transmit energy sufficient to excite an acceptor fluorophore.

As used herein, the term "fluorescent dye" refers to a non-polypeptide chemical moiety that, upon absorption of light energy of a particular wavelength or wavelengths, emits light at another wavelength or that emits light when paired with an appropriate excited donor fluorophore.

When referring to members of a pair of fluorophores (i.e., fluorescent dyes or polypeptides) that can undergo fluorescence resonance energy transfer (FRET), the fluorophore that emits at a wavelength or spectrum of wavelengths that excites the other member of the pair is referred to as the "fluorescent donor" or "fluorescence donor". Conversely, the member of the pair that emits in response to excitation by the fluorescence donor is termed the "fluorescent acceptor" or "fluorescence acceptor". The members of such a pair are said to be "fluorescent donor and acceptor to each other." According to the invention, the fluorescence donor and fluorescence acceptor polypeptides are not linked by peptide bonds. In one embodiment of the invention, either of the fluorescence donor or acceptor, but not both, may be a non-polypeptide fluorescent dye (also not covalently linked to each other).

As used herein, the term "fluorescently labeled" means, when referring to a polypeptide, that the polypeptide is covalently attached to a fluorescent moiety. A polypeptide may be fluorescently labeled by covalent attachment to a non-polypeptide fluorescent dye, or alternatively, by expression as a fusion protein with a fluorescent polypeptide.

In nature and as used herein, a fluorescent polypeptide is distinguished from a luminescent polypeptide in that a fluorescent polypeptide requires an input of electromagnetic energy in order to emit light, while a luminescent polypeptide emits light in response to release of chemical energy. A luminescent polypeptide may serve as a donor of excitation, energy for a fluorescent polypeptide (in fact, this is exactly what happens in nature when, for example, *Renilla* luciferase emits energy that excites *Renilla* GFP). A fusion polypeptide according to the invention may or may not be luminescent.

As used herein, the term "recombinant" refers to a polynucleotide that has been isolated from its natural environment using recombinant DNA techniques, or synthesized, or to a polypeptide expressed from such a polynucleotide. A recombinant polypeptide may be identical to or different from a naturally occurring polypeptide, as long as it is expressed from a recombinant polynucleotide.

As used herein, the term "monomer" refers to a single polypeptide molecule that exists as a dimer or heterodimer or other multimer (e.g., a trimer, quadramer, pentamer, etc.) in a multimeric protein. A "monomer" interacts with another monomer, e.g., in a dimer, via a specific sequence referred to herein by the equivalent terms "interaction domain" and "interaction interface". In a "dimer" the appropriate equivalent terms for the sequences that mediate the interaction are "dimerization domain" and "dimerization interface."

A monomer of a fluorescent polypeptide may be full length, for example, as the polypeptide occurs in nature, or it may be longer or shorter than the naturally occurring polypeptide, so long as it retains the two requisite properties.

A recombinant fusion polypeptide according to the invention may comprise first and second polypeptides which exist in nature as non-peptide-bonded monomers of a multimeric protein. Thus, the term "monomer" is used with respect to what is found in nature.

In a fusion polypeptide according to the invention, these first and second polypeptides are peptide bonded and form a single chain polypeptide. However, the peptide-bonded first and second polypeptides retain the ability, independently, to interact with a donor or acceptor fluorophore and fluoresce. This is believed to be a result of the intramolecular interaction of the monomers and the ability of the intramolecular dimer thus formed to be excited at an excitation wavelength of light and to act as a fluorescent donor or acceptor.

As used herein, the term "linker sequence" refers to a sequence of peptide bonded amino acids that joins or links by peptide bonds two amino acid sequences or polypeptide domains that are not joined by peptide bonds in nature. A linker sequence is encoded in frame on a polynucleotide between the sequences encoding the two polypeptide domains joined by the linker. A linker is preferably 5 to 50 amino acids in length, more preferably 10 to 20 amino acids in length. An example of linkers useful in the invention are the Gly-Ala linkers taught by Huston et al., U.S. Pat. No. 5,258,498, incorporated herein by reference. Additional useful linkers include, but are not limited to (Arg-Ala-Arg-Asp-Pro-Arg-Val-Pro-Val-Ala-Thr)$_{1-5}$ (SEQ ID NO: 8; Xu et al., 1999, Proc. Natl. Acad. Sci. U.S.A. 96: 151–156), (Gly-Ser)$_n$ (Shao et al., 2000, Bioconjug. Chem. 11: 822–826), (Thr-Ser-Pro)$_n$ (Kroon et al., 2000, Eur. 3. Biochem. 267: 6740–6752), (Gly-Gly-Gly)$_n$ (Kluczyk et al., 2000, Peptides 21: 1411–1420), and (Glu-Lys)$_n$ (Klyczyk et al., 2000, supra), wherein n is 1 to 15.

As used herein, the term "specific binding pair" refers to a pair of polypeptides that physically interact in a specific manner that gives rise to a biological activity, that is, to the substantial exclusion of other polypeptides. Members of a specific binding pair interact through complementary interaction domains, such that they interact to the substantial exclusion of proteins that do not have a complementary interaction domain. Non-limiting examples of specific binding pairs include antibody-antigen pairs, enzyme-substrate pairs, dimeric transcription factors (e.g., AP-1, composed of Fos specifically bound to Jun via a leucine zipper interaction domain) and receptor-ligand pairs.

As used herein, the term "amino terminus" refers to the last amino acid at the amino end of a polypeptide, where the last amino acid is not peptide bonded to another amino acid.

As used herein, the term "carboxy terminus" refers to the last amino acid at the carboxyl end of a polypeptide, where the last amino acid is not peptide bonded to another amino acid.

As used herein, the term "labeling a cell" refers to the expression of a fluorescent polypeptide in a cell, such that the cell is detectable by irradiating the cell with light within the excitation spectrum of the fluorescent polypeptide and monitoring or detecting emission within the emission spectrum of the polypeptide. A cell may be labeled by expression of a fluorescent polypeptide that localizes anywhere in the cell, including, but not limited to the cell surface, the cytoplasm, the nucleus or to particular organelles such as mitochondria, lysosomes, endosomes, golgi apparatus, endoplasmic reticulum or other specific sub-cellular locale.

As used herein, the term "introducing a nucleic acid into a cell" or "introducing a polynucleotide into a cell" refers to the process whereby a recombinant polynucleotide is put into a cell. Methods for introducing a nucleic acid to a cell will vary with the nature of the cell and the nature of the chosen vector, but one of skill in the art may readily select and employ a known method appropriate for a given cell type and vector.

As used herein, the term "culturing a cell under conditions that permit the synthesis of a recombinant polypeptide" refers to the maintenance of cells comprising a polynucleotide encoding a recombinant polypeptide in growth medium and under environmental conditions (e.g., temperature, pH, redox and osmotic conditions, $O_2$ and $CO_2$ concentrations and presence or absence of an effective concentration of an appropriate expression-modulating agent such as IPTG or tetracycline) conducive to the synthesis of the recombinant polypeptide. One of skill in the art is assumed to be capable of maintaining yeast, insect, mammalian or other cells under conditions that permit the synthesis of a recombinant polypeptide according to the invention.

As used herein, the term "monitoring the interaction" refers to the process whereby the physical association of two polypeptides or a polypeptide and another entity are measured. As relates to the invention, the term refers most frequently to detection or measurement of association or interaction using FRET.

As used herein, the term "intramolecular dimer" refers to a dimer formed by the covalent peptide linkage of two polypeptide monomers. An "intramolecular dimer fluorescent protein" (IDFP) is an intramolecular dimer in which the linked polypeptides which exist in nature as monomers of a multimeric protein are fluorescent polypeptides. According to the invention, the linked monomers of an IDFP are not fluorescent donor and acceptor to each other. An "IDFP fusion protein" is an IDFP which is fused to a protein of interest or to a fragment of a protein of interest.

As used herein, the term "protein of interest" refers to a polypeptide, or a domain (fragment) of a polypeptide, that is selected to be fused to an IDFP. Any polypeptide or fragment of a polypeptide for which a polynucleotide sequence is known can be fused to an IDFP by standard techniques known in the art. A protein of interest according to the invention either does not alter the fluorescence characteristics of the fused IDFP, or, if it does alter those characteristics, the alteration is such that the alteration does not interfere with the intended use of the IDFP fusion protein.

As used herein, the term "detecting fluorescence" refers to the process whereby the fluorescent emission by a fluorescent polypeptide is measured or determined. Fluorescence detection methods include quantitative and qualitative methods adapted for standard or confocal microscopy, FACS analysis, and those adapted for high throughput methods involving multiwell plates, arrays or microarrays. One of skill in the art can select appropriate filter sets and excitation energy sources for the detection of fluorescent emission from a given fluorescent polypeptide or dye.

As used herein, the term "candidate modulator" refers to an agent being evaluated for its effect on the function of a polypeptide or the interaction of members of a specific binding pair. Exemplary sources and types of candidate modulators useful according to the invention are described herein below.

As used herein, the term "change in interaction" or "modulation of interaction" refers to an increase or decrease in the level of interaction detected between members of a specific binding pair. As used herein, the level of interaction is considered increased if the detected interaction goes up by at least 10%, and preferably by 20%, 35%, 50%, 75%, or more, up to and including 2-fold, 5-fold, 10-fold, 20-fold, 50-fold or more relative to a standard. As used herein, the level of interaction is considered decreased if the detected interaction goes down by at least 10%, and preferably by 20%, 35%, 50%, 75%, 90%, 95%, 98%, 99% or more, up to and including 100% (no interaction) relative to a standard.

As used herein, the term "single polypeptide chain" refers to a polypeptide chain in which all amino acids are linked sequentially by peptide bonds. A "single polypeptide chain" is one generated by translation of a single mRNA template and may encompass one or more polypeptide domains, including one or more repeats of the sequence comprising one polypeptide or polypeptide domain.

As used herein, the term "polypeptide domain" refers to a sequence of amino acids that exhibits one or more discrete binding or functional properties. As used herein, binding or functional properties include binding to one or more polypeptides, modulation of the binding of one or more polypeptides, recognition by an antibody or antigen binding fragment thereof binding to a coenzyme, ion, or other ligand, catalytic activity or inhibition of catalytic activity, fluorescence and luminescence. In this context, non-limiting examples of polypeptide domains include a DNA binding domain and a kinase domain.

As used herein, the term "homodimer" refers to a protein complex comprised of two identical copies of the same monomer.

As used herein, the term "interact" means that two molecular species physically associate with each other. The association that is characterized as an interaction can involve charge-charge interactions, charge-dipole interactions, dipole-dipole interactions, van der Waals forces, hydrogen bonding and/or hydrophobic forces.

As used herein, the term "specific binding" means the specific recognition of one of two different molecules for the other compared to substantially less recognition of other molecules. Members of a specific binding pair have a particular affinity for each other that gives rise to a biological activity. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

As used herein, the term "specifically dimerize" means that two monomers useful in the invention interact via an interaction domain present on each monomer, to the substantial exclusion of polypeptides lacking that interaction domain. "Specifically homodimerize" means that the monomers that interact via a shared interaction domain, to the substantial exclusion of polypeptides lacking that interaction domain, form a homodimer as defined, herein. "Substantial exclusion" means that at a given time in a sample, less than 0.1% of the monomers, and preferably less than 0.01%, 0.001% or fewer monomers are physically associated with polypeptides that do not have a complementary interaction domain.

As used herein, the term "variant" refers to a polypeptide that differs in amino acid, sequence from a parent polypeptide yet retains the function of the parent polypeptide. A variant fluorescent polypeptide may, for example, have one or more amino acid insertions, deletions or substitutions that do not alter ability of the polypeptide to emit fluorescence upon excitation or interaction with a donor or acceptor fluorophore. A variant fluorescent polypeptide according to the invention has the ability to form an intramolecular homodimer as defined herein.

As used herein, the term "derived from" refers to a polypeptide that differs in amino acid sequence from a reference polypeptide used as the template or starting sequence for generating or deriving the differing sequence. For example, a fluorescent polypeptide can be derived from a, wild-type fluorescent polypeptide (i.e., a reference polypeptide) by random or site-directed mutagenesis, including insertions, deletions or truncations or fusions. A fluorescent polypeptide derived from a wild-type polypeptide can have different fluorescence characteristics than the wild-type polypeptide.

As used heroin, the term "fluorescence characteristic", refers to a property of the excitation or emission by a fluorescent polypeptide. Fluorescence characteristics include, for example, the wavelength(s) at which a fluorescent polypeptide is excited or at which it emits (including the breadth and amplitudes of the spectra for each), the extinction coefficient or intensity of the emission, quantum yield or the efficiency of emission, and resistance or susceptibility to photobleaching. Table 2 provides examples of excitation maxima, emission maxima, extinction coefficient and quantum yield for a variety of fluorescent polypeptides.

As used herein, the term "spectrum characteristic of a fluorescent acceptor" refers to the emission spectrum of a given fluorophore that is being used as the fluorescence acceptor in an acceptor/donor pair.

Detailed Description of the Invention

In one aspect, the invention relates to dimeric fluorescent proteins that avoid the problems caused by heterodimerization. In this aspect, heterodimerization is avoided by fusing two monomers of the fluorescent polypeptide using a linker peptide. The close spatial relationship of the fused monomers strongly favors the formation of a dimer between the two fused monomers, to the essential exclusion of other monomers sharing a similar dimerization interface. The interaction of the fused monomers via their respective dimerization interfaces is referred to herein as "intramolecular dimerization". An intramolecular dimer fluorescent protein (IDFP) does not comprise fluorescent monomers that are related to each other as donor and acceptor. That is, the monomers that are linked in an IDFP cannot undergo FRET between them. IDFPs may be co-expressed within the same cell or otherwise mixed with distinct fluorescent proteins comprising the same fluorescent protein dimerization interfaces without encountering the problems caused by heterodimer formation.

In order to make an IDFP, the nucleic acid encoding a monomer of a fluorescent protein is joined in frame at its 3' end to a sequence encoding a peptide linker, which is itself joined in frame to another copy of the nucleic acid encoding the monomer. This sequence may and often will be additionally linked in frame to a sequence encoding a polypeptide of interest, for example, a polypeptide being investigated for interaction with another protein. Translation of the mRNA encoded by such a nucleic acid construct generates the fluorescent monomers in such close proximity to each other that intramolecular homodimerization of the monomers is very strongly favored over intermolecular heterodimerization. The resulting polypeptide, therefore comprises an intramolecular homodimer of the fluorescent protein monomers, fused to a protein of interest.

Fluorescent Proteins Useful According to the Invention

Any fluorescent protein that homodimerizes in a cell can be useful in generating an IDFP of the invention. GFPs from *Aequorea victoria, Renilla reniformis* and *Renilla mulleri,* among others, are homodimers as they exist in nature. Any of these proteins, and any mutants or engineered versions of these proteins that retain the ability to homodimerize may be used to generate an IDFP of the invention.

In order to generate an IDFP according to the invention, the fluorescent protein or the natural protein it was derived from (e.g., *R. reniformis* GFP) must form homodimers when expressed in a monomeric form. It is generally known in the field whether a given protein exists as a homo- or heterodimer in vivo or if it has the capacity to homodimerize. In the event that such knowledge is not available, there are a number of ways in which one of skill in the art may determine whether a particular fluorescent protein homodimerizes. First, biophysical methods such as X-ray crystallography, nuclear magnetic resonance, radiation target analysis or mass spectrometry can be used to determine whether a polypeptide dimerizes.

A biochemical approach is to fractionate samples of purified proteins by size selection gel chromatography under denaturing versus non-denaturing conditions and analyze fractions for the fluorescent protein by fluorescence. If the fluorescent protein migrates at a larger size (approximately twice as large) under non-denaturing conditions relative to denaturing conditions, it is an indication that the protein is a dimer under native conditions. Examples of commonly used matrices include, for example, Sephadex (G10–G200), Bio-Gel (P2–P-300) and Sepharose (2B, 4B, etc.) matrices. One of skill in the art may readily, select a size separation matrix appropriate for such analyses. If performed with purified protein this method can indicate whether or not a polypeptide homodimerizes. If the method is applied to non-purified protein, for example, to protein extracts, the assay only indicates that a dimer forms with some polypeptide, and further analysis is required to determine if the dimer is a homodimer.

Another biochemical method of investigating dimer formation is to generate a truncated or elongated form of the protein and mix it, either by co-expression or by mixing of isolated proteins, with the wild-type protein. If homodimers can form, there will be three distinctly sized bands following native gel electrophoresis: 1) a homodimer of the wild-type; 2) a homodimer of the elongated or truncated form; and 3) an intermediate-migrating diagnostic heterodimer complex of the wild-type and the truncated forms. In the absence of dimerization, only bands (1) and (2) will form.

Additionally, homodimer formation is detected by the method of analytical ultracentrifugation (Baird et al., 2000, Proc Natl Acad Sci U S A., 22:11984–9).

Examples of known fluorescent proteins that can be expressed as intramolecular dimers are as follows. SEQ ID NO: 1 (FIG. 1) is the nucleotide sequence encoding wild-type rGFP, and SEQ ID NO: 2 (FIG. 2) is the amino acid sequence of wild-type rGFP. A preferred embodiment of the IDFP comprises two copies of the wild-type rGFP polypeptide, linked by a peptide linker sequence. Another embodiment encompasses the same rGFP IDFP additionally fused in frame to a protein of interest. Any protein derived from the rGFP of SEQ ID NO: 2 can be used to generate an IDFP of the invention as long as it retains the ability to homodimerize. In a preferred embodiment, the polynucleotide sequence encoding a fluorescent polypeptide (e.g., rGFP of SEQ ID NO: 2) is a humanized polynucleotide rGFP coding sequence, also referred to herein as hrGFP. FIG. 3 shows a humanized polynucleotide sequence (hrGFP) and the rGFP sequence it encodes (SEQ ID Nos: 3 and 4, respectively).

The amino acid and nucleotide sequences of *A. Victoria* GFP are known in the art (Prasher et al., 1992, supra) and vectors encoding a variety of mutant *A. victoria*-derived GFPs are also known and are frequently commercially available. For example, Heim et al. (1995, Nature 373: 663–664) teaches mutations at S65 of *A. victoria* GFP that enhance the fluorescence intensity of the polypeptide. The mutant containing the S65T mutation is particularly important, since its fluorescence is approximately 35 times as intense as wild-type *A. victoria* GFP, and its emission spectrum is shifted to the red, making it more amenable to standard rhodamine optics (excitation and emission maxima at 489 nm and 508 nm, respectively). An S65T mutant encoded by a construct comprising humanized codons is known as EGFP, or “enhanced GFP” (available from CLONTECH; see GenBank Accession No. U43284).

The EGFP mutant is the cornerstone of a series of commercially-available GFP mutants that have differing emission spectra and other useful engineered properties (Cormack et al., 1996, Gene 173: 33–38; Yang et al., 1996, Nucl. Acids Res. 24: 4592–4593; Crameri et al., 1996, Nature Biotechnol. 14: 315–319). Each protein in the series contains mutations in addition to the S65T and humanizing mutations, that alter the emission characteristics of the proteins. For example, the cyan fluorescent protein known as ECFP contains six mutations that shift the emission to cyan light (excitation and emission maxima at 434 nm and 477 nm, respectively; see GenBank Accession No. AB041904 and Sawano et al., 2000, Nucl. Acids Res. 28: e78). The blue fluorescent protein known as EBFP contains four mutations that shift the emission spectrum to blue (excitation and emission maxima at 380 nm and 440 nm, respectively). The yellow fluorescent protein known as EYFP (see Ormo et al., Science 273: 1392–1395, clone GFP-10C) contains mutations shifting the emission, to yellow-green (excitation and emission maxima at 514 nm and 527 nm, respectively). EGFP, ECFP, EYFP and EBFP are all available from CLONTECH.

The S65 site has received considerable scrutiny for its role in determining the fluorescence characteristics of the *A. victoria* GFP molecule. Additional mutants at S65 include, for example, S65A, S65C and S65L, each of which have excitation and emission maxima that differ from wild-type *A. victoria* GFP (see Table 2). The nucleotide sequence encoding an S65A mutant is available as GenBank Accession No. U56996. One skilled in the art can introduce mutations necessary to alter S65 to any desired amino acid. Similarly, the additional point mutations detailed in Table 2 can be generated by one of skill in the art.

Other fluorescent proteins useful according to the invention include, for example, *A. victoria*-derived GFPs that are optimized for expression in plants (GenBank Accession No. U87625 and WO 96/27675), are less thermosensitive (GenBank Accession No. U87973), or are more soluble and emit blue fluorescence (GenBank Accession No. U70497). *A. victoria* GFPs targeted to specific organelles have also been described, such as those targeted to the mitochondria and the nucleus (Rizzuto et al., 1996, Curr. Biol. 6: 183–188). This, listing is by no means exhaustive. There are, for example, a number of fluorescent protein variants, both derived from *A. victoria* and from other sources, that have been reported in or are the subject of U.S. and international patents and patent applications, for example, U.S. Pat. Nos. 6,124,128, 6,066,476, 6,020,192, 5,804,387, 5,874,304, 5,968,738, 5,625,048, and 5,777,079, and PCT Application Nos. WO 98/21355, WO 98/06737, WO 97/20078, WO 97/42320 and WO 97/11094. Fluorescent protein variants are also described in a number of additional publications in the scientific literature, including, for example, Ehrig et al., 1995, FEBS Lett. 367: 163–166); Surpin et al., 1987, Photochem. Photobiol. 45 (Suppl): 95S; and Delagrave et al., 1995, BioTechnology 13: 151–154. Any and all of the fluorescent proteins taught in these sources and elsewhere are candidates for the generation of IDFPs of the invention., provided that they homodimerize and the sequences encoding them are known.

The red fluorescent protein from the Indo-Pacific sea anemone of the *Discosoma* species is also a candidate for IDFP generation according to the invention (see Matz et al, 1999, Nature Biotechnol. 17: 969–973). The sequence encoding the protein, known as “DsRed” is available at GenBank Accession No. AF27271 1, and vectors encoding the protein are commercially available (CLONTECH).

Linker Sequences Useful According to the Invention

Linker sequences useful according to the invention serve to join monomers in the dimeric fluorescent polypeptides of the invention. A linker is preferably about 5 to about 50 amino acids in length, and more preferably about 10 to about 20 amino acids in length. An example of linkers useful in the invention are the Gly-Ala linkers taught by Huston et al., U.S. Pat. No. 5,258,498, incorporated herein by reference. Additional useful linkers include, but are not limited to $(\text{Arg-Ala-Arg-Asp-Pro-Arg-Val-Pro-Val-Ala-Thr})_{1\text{-}5}$(SEQ ID NO: 8; Xu et al., 1999, Proc. Natl. Acad. Sci. U.S.A. 96: 151–156), $(\text{Gly-Ser})_n$(Shao et al., 2000, Bioconjug. Chem. 11: 822–826), $(\text{Thr-Ser-Pro})_n$(Kroon et al., 2000, Eur. J. Biochem. 267: 6740–6752), $(\text{Gly-Gly-Gly})_n$(Kluczyk et al., 2000, Peptides 21:1411–1420), and $(\text{Glu-Lys})_n$(Klyczyk et al., 2000, supra), wherein n is 1 to 15 (each of the preceding references is also incorporated herein by reference).

Proteins of Interest

Frequently it will be advantageous to express an IDFP of the invention as a fusion with a protein of interest. The protein of interest can be any protein for which the nucleic acid sequence is known and for which that sequence or at least a relevant part of that sequence can be cloned into a vector encoding an IDFP. By relevant part is meant a domain of interest within a protein, for example, a domain being evaluated for protein:protein interactions or a domain with catalytic activity. As used herein, the term “protein of interest” or “domain of interest” refers to any polypeptide or protein, or polypeptide or protein domain, that one wishes to fuse to an IDFP molecule of the invention. The fusion of an IDFP with a polypeptide of interest may be through linkage of the IDFP sequence to either the N or C terminus of the fusion partner. Fusions comprising IDFP polypeptides of the invention need not comprise only a single polypeptide or domain in addition to the IDFP. Rather, any number of domains of interest may be linked in any way as long as the IDFP coding region retains its reading frame and the encoded polypeptide retains fluorescence activity under at least one set of conditions. One non-limiting example of such conditions includes physiological salt concentration (i.e., about 90 mM), pH near neutral and 37° C.

Examples of proteins of interest include, but are not limited to receptors (transmembrane and intracellular) and cell surface proteins, growth factors, signal transduction proteins, transcription factors, structural proteins (e.g., cytoskeletal proteins, nuclear matrix proteins, histones, etc.), extracellular matrix proteins, immunoglobulins, bacterial proteins, plant proteins, viral or phage proteins, enzymes, therapeutic proteins, phosphoproteins, glycoproteins, and lipoproteins.

Production of Intramolecular Dimer Fluorescent Proteins

The production of IDFPs from recombinant vectors may be effected in a number of ways known to those skilled in the art. For example, plasmids, bacteriophage or viral vectors may be introduced to prokaryotic or eukaryotic cells by any of a number of ways known to those skilled in the art. Examples of useful vectors, cells, methods of introducing vectors to cells and methods of detecting and isolating GFP polypeptides and variants thereof are also described herein below.

1. Vectors Useful According to the Invention.

There is a wide array of vectors known and available in the art that are useful for the expression of IDFPs according to the invention. The selection of a particular vector clearly depends upon the intended use of the polypeptide. For example, the selected vector must be capable of driving expression of the polypeptide in the desired cell type, whether that cell type be prokaryotic or eukaryotic. Many vectors comprise sequences allowing both prokaryotic vector replication and eukaryotic expression of operably linked gene sequences.

Vectors useful according to the invention may be autonomously replicating, that is, the vector, for example, a plasmid, exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors.

Vectors useful according to the invention preferably comprise sequences operably linked to the IDFP coding sequences that permit the transcription and translation of the IDFP sequence. Sequences that permit the transcription Of the linked IDFP sequence include a promoter and optionally also include an enhancer element or elements permitting the strong expression of the linked sequences. The term "transcriptional regulatory sequences" refers to the combination of a promoter and any additional sequences conferring desired expression characteristics (e.g., high level expression, inducible expression, tissue- or cell-type-specific expression, or a combination of these) on an operably linked nucleic acid sequence.

The selected promoter may be any DNA sequence that exhibits transcriptional activity in the selected host cell, and may be derived from a gene normally expressed in the host cell or from a gene normally expressed in other cells or organisms. Examples of promoters include, but are not limited to the following: A) prokaryotic promoters—*E. coli* lac, tac, or trp promoters, lambda phage $P_R$ or $P_L$ promoters, bacteriophage T7, T3, Sp6 promoters, *B. subtilis* alkaline protease promoter, and the *B. stearothermophilus* maltogenic amylase promoter, etc.; B) eukaryotic promoters—yeast promoters, such as GAL1, GAL4 and other glycolytic gene promoters (see for example, Hitzeman et al., 1980, J. Biol. Chem. 255: 12073–12080; Alber & Kawasaki, 1982, J. Mol. Appl. Gen. 1: 419–434), LEU2 promoter (Martinez-Garcia et al., 1989, Mol Gen Genet. 217: 464–470), alcohol dehydrogenase gene promoters (Young et al., 1982, in Genetic Engineering of Microorganisms for Chemicals, Hollaender et al., eds., Plenum Press, NY), or the TPI1 promoter (U.S. Pat. No. 4,599,311); insect promoters, such as the polyhedrin promoter (U.S. Pat. No. 4,745,051; Vasuvedan et al., 1992, FEBS Lett. 311: 7–11), the P10 promoter (Vlak et al., 1988, J. Gen. Virol. 69: 765–776), the *Autographa californica* polyhedrosis virus basic protein promoter (EP 397485), the baculovirus immediate-early gene promoter gene 1 promoter (U.S. Pat. Nos. 5,155,037 and 5,162,222), the baculovirus 39K delayed-early gene promoter (also U.S. Pat. Nos. 5,155,037 and 5,162,222) and the OpMNPV immediate early promoter 2; mammalian promoters—the SV40 promoter (Subramani et al., 1981, Mol. Cell. Biol, 1: 854–864), metallothionein promoter (MT-1; Palmiter et al., 1983, Science 222: 809–814), adenovirus 2 major late promoter (Yu et al., 1984, Nucli. Acids Res. 12: 9309–21), cytomegalovirus (CMV) or other viral promoter (Tong et al., 1998, Anticancer Res. 18: 719–725), or even the endogenous promoter of a gene of interest in a particular cell type.

A selected promoter may also be linked to sequences rendering it inducible or tissue-specific. For example, the addition of a tissue-specific enhancer element upstream of a selected promoter may render the promoter more active in a given tissue or cell type. Alternatively, or in addition, inducible expression may be achieved by linking the promoter to any of a number of sequence elements permitting induction by, for example, thermal changes (temperature sensitive), chemical treatment (for example, metal ion- or IPTG-inducible), or the addition of an antibiotic inducing agent (for example, tetracycline).

Regulatable expression is achieved using, for example, expression systems that are drug inducible (e.g., tetracycline, rapamycin or hormone-inducible). Drug-regulatable promoters that are particularly well suited for use in mammalian cells include the tetracycline regulatable promoters, and glucocorticoid steroid-, sex hormone steroid-, ecdysone-, lipopolysaccharide (LPS)- and isopropylthiogalactoside (IPTG)-regulatable promoters. A regulatable expression system for use in mammalian cells should ideally, but not necessarily, involve a transcriptional regulator that binds (or fails to bind) nonmammalian DNA motifs in response to a regulatory agent, and a regulatory sequence that is responsive only to this transcriptional regulator;

Tissue-specific promoters may also be used to advantage with IDFP-encoding constructs. A wide variety of tissue-specific promoters is known. As used herein, the term "tissue-specific" means that a given promoter is transcriptionally active (i.e., directs, the expression of linked sequences sufficient to permit detection of the polypeptide product of the promoter) in less than all cells or tissues of an organism. A tissue specific promoter is preferably active in only one cell type, but may, for example, be active in a particular class or lineage of cell types (e.g., hematopoietic cells). A tissue specific promoter useful according to the invention comprises those sequences necessary and sufficient for the expression of an operably linked nucleic acid sequence in a manner or pattern that is essentially the same as the manner or pattern of expression of the gene linked to that promoter in nature. Any tissue specific transcriptional regulatory sequence known in the art may be used to advantage with a vector encoding an IDFP.

In addition to promoter/enhancer elements, vectors useful according to the invention may further comprise a suitable terminator. Such terminators include, for example, the human growth hormone terminator (Palmiter et al., 1983, supra), or, for yeast or fungal hosts, the TPI1 (Alber & Kawasaki, 1982, supra) or ADH3 terminator (McKnight et al., 1985, EMBO J. 4:2093–2099).

Vectors useful according to the invention may also comprise polyadenylation sequences (e.g., the SV40 or Ad5E1b poly(A) sequence), and translational enhancer sequences (e.g., those from Adenovirus VA RNAs). Further, a vector useful according to the invention may encode a signal sequence directing the recombinant polypeptide to a particular cellular compartment or, alternatively, may encode a signal directing secretion of the recombinant polypeptide.

A vector useful according to the invention may also comprise a selectable marker allowing identification of a cell that has received a functional copy of the IDFP-encoding gene construct. In its simplest form, the IDFP sequence itself, linked to a chosen promoter may be considered a selectable marker, in that illumination of cells or cell lysates with the proper wavelength of light and measurement of emitted fluorescence at the expected wavelength allows detection of cells that express the IDFP construct. In other forms, the selectable marker may comprise an antibiotic resistance gene, such as the neomycin, bleomycin, zeocin or phleomycin resistance genes, or it may comprise a gene whose product complements a defect in a host cell, such as the gene encoding dihydrofolate reductase (DHFR), or, for example, in yeast, the Leu2 gene. Alternatively, the selectable marker may, in some cases be a luciferase gene or a chromogenic substrate-converting enzyme gene such as the β-galactosidase gene.

IDFP-encoding sequences according to the invention may be expressed either as freestanding polypeptides or as fusions with other polypeptides. It is assumed that one of skill in the art can, given an IDFP nucleic acid sequence, readily construct a gene comprising a sequence encoding the IDFP fused in frame to one or more polypeptides or polypeptide domains of interest. References teaching methods to do so include Sambrook et al., 1989, *Molecular Cloning, A Laboratory Manual,* Cold Spring Harbor Laboratory Press, Cold Spring Harbor, N.Y., and Ausubel et al. (eds.), 1993, *Current Protocols in Molecular Biology on CD-ROM,* John Wiley & Sons, New York, N.Y.

A schematic diagram of a vector encoding the transcription unit of one possible embodiment of the invention is shown in FIG. 4. In this embodiment, an intramolecular dimer humanized *R. reniformis* GFP (hrGFP) is encoded on a construct driven by the strong CMV promoter and containing a multi-cloning site (MCS) downstream of the second, or C-terminal copy of hrGFP. A gene of interest is fused at the C-terminus of the hrGFP dimer by insertion in frame into the MCS. A polyadenylation site sequence is included 3' of the MCS to enhance the stability and processing of the transcript generated. The $(Gly_4Ser)_{2-4}$ linkers shown represent three examples of a linker peptide sequence useful according to the invention and are not meant to be limiting.

a. Plasmid Vectors.

Any plasmid vector that allows expression of an IDFP coding sequence of the invention in a selected host cell type is acceptable for use according to the invention. A plasmid vector useful in the invention may have any or all of the above-noted characteristics of vectors useful according to the invention. Plasmid vectors useful according to the invention include, but are not limited to the following examples: Bacterial—pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKX233-3, pDR540, and pRIT5 (Pharmacia); Eukaryotic—pWLneo, pSV2cat, pOG44, pXT1, pSG (Stratagene) pSVK3, pBPV, pMSG, and pSVL (Pharmacia). However, any other plasmid or vector may be used as long as it is replicable in the host.

b. Bacteriophage Vectors.

There are a number of well known bacteriophage-derived vectors useful according to the invention. Foremost among these are the lambda-based vectors, such as Lambda Zap II or Lambda-Zap Express vectors (Stratagene) that allow inducible expression of the polypeptide encoded by the insert. Others include filamentous bacteriophage such as the M13-based family of vectors.

c. Viral Vectors.

A number of different viral vectors are useful according to the invention, and any viral vector that permits the introduction and expression of sequences encoding an IDFP in cells is acceptable for use in the methods of the invention. Viral vectors that can be used to deliver foreign nucleic acid into cells include but are not limited to retroviral vectors, adenoviral vectors, adeno-associated viral vectors, herpesviral vectors, and Semliki forest viral (alphaviral) vectors. Defective retroviruses are well characterized for use in gene transfer (for a review see Miller, A. D. (1990) *Blood* 76:271). Protocols for producing recombinant retroviruses and for infecting cells in vitro or in vivo with such viruses can be found in Ausubel et al. (eds.), 1993, supra, and other standard laboratory manuals.

In addition to retroviral vectors, adenoviruses can be manipulated such that they encode and express a gene product of interest but are inactivated in terms of their ability to replicate in a normal lytic viral life cycle (see for example Berkner et al., 1988, BioTechniques 6:616; Rosenfeld et al., 1991, Science 252:431–434; and Rosenfeld et. al., 1992, Cell 68:143–155). Suitable adenoviral vectors derived from the adenovirus strain Ad type 5 d1324 or other strains of adenovirus (e.g., Ad2, Ad3, Ad7 etc.) are well known to those skilled in the art. Adeno-associated virus (AAV) is a naturally occurring defective virus that requires another virus, such as an adenovirus or a herpes virus, as a helper virus for efficient replication and a productive life cycle. (For a review see Muzyczka et al., 1992, Curr. Topics in Micro. and Immunol. 158:97–129). An AAV vector such as that described in Traschin et al. (1985, Mol. Cell. Biol. 5:3251–3260) can be used to introduce nucleic acid into cells. AAV vectors are useful for the introduction of nucleic acid sequences into a variety of different cell types (see, for example, Hermonat et al., 1984, Proc. Natl. Acad. Sci. USA 81: 6466–6470; and Traschin et al., 1985, Mol. Cell. Biol. 4:2072–2081).

Finally, the introduction and expression of foreign genes is often desired in insect cells because high level expression may be obtained, the culture conditions are simple relative to mammalian cell culture, and the post-translational modifications made by insect cells closely resemble those made by mammalian cells. For the introduction of foreign DNA to insect cells, such as Drosophila S2 cells, infection with baculovirus vectors is widely used. Other insect vector systems include, for example, the expression plasmid pIZ/V5-His (InVitrogen) and other variants of the pIZ/V5 vectors encoding other tags and selectable markers. Insect cells are readily transfectable using lipofection reagents, and there are lipid-based transfection products specifically optimized for the transfection of insect cells (for example, from PanVera).

2. Host Cells Useful According to the Invention.

Any cell into which a recombinant vector carrying an IDFP sequence may be introduced and wherein the vector is permitted to drive the expression of the IDFP is useful according to the invention. That is, because of the wide variety of uses for the IDFP molecules of the invention, any cell in which an IDFP molecule of the invention may be expressed and preferably detected is a suitable host. Vectors suitable for the introduction of IDFP-encoding sequences to host cells from a variety of different organisms, both prokaryotic and eukaryotic, are described herein above or known to those skilled in the art.

Host cells may be prokaryotic, such as any of a number of bacterial strains, or may be eukaryotic, such as yeast or other fungal cells, insect or amphibian cells, or mammalian cells including, for example, rodent, simian or human cells. Host cells may also be plant cells. Cells expressing IDFPs may be primary cultured cells, for example, primary human fibroblasts or keratinocytes, or may be an established cell line, such as NIH3T3, 293T or CHO cells. Further, mammalian cells useful for expression of IDFPs may be phenotypically normal or oncogenically transformed. It is assumed that one skilled in the art can readily establish and maintain a chosen host cell type in culture.

3. Introduction of IDFP-Encoding Vectors to Host Cells.

IDFP-encoding vectors may be introduced to selected host cells by any of a number of suitable methods known to those skilled in the art. For example, IDFP constructs may be introduced to appropriate bacterial cells by infection, in the case of *E. coli* bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, supra), but electroporation may also be used (Ausubel et al. (eds.), supra, 1993).

For the introduction of IDFP-encoding constructs to yeast or other fungal cells, chemical transformation methods are generally used (e.g. as described by Rose et al., 1990, *Methods in Yeast Genetics,* Cold Spring Harbor Laboratory Press, Cold Spring Harbor, N.Y.). For transformation of *S. cerevisiae,* for example, the cells are treated with lithium acetate to achieve transformation efficiencies of approximately $10^4$ colony-forming units (transformed cells)/$\mu$g of DNA. Transformed cells are then isolated on selective media appropriate to the selectable marker used. Alternatively, or in addition, plates or filters lifted from plates may be scanned for IDFP fluorescence to identify transformed clones.

For the introduction of IDFP-encoding vectors to mammalian cells, the method used will depend upon the form of the vector. For plasmid vectors, DNA encoding an IDFP may be introduced by any of a number of transfection methods, including, for example, lipid-mediated transfection ("lipofection"), DEAE-dextran-mediated transfection, electroporation or calcium phosphate precipitation. These methods are detailed, for example, in Ausubel et al. (eds.), 1993, supra.

Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

For the introduction of IDFP-encoding vectors to insect cells, liposome-mediated transfection is commonly used, as is baculovirus infection. Cells such as Schneider-2 cells (*Drosophila melanogaster*), Sf-9 and Sf-21 cells (*Spodoptera frugiperda*) or High Five™ cells (*Trichoplusia ni*) may be transfected using any of a number of commercially available liposome transfection reagents optimized for use with insect cells. Reagents include, for example, TransIT-Insecta™ (PanVera), FU GENE™-6 (Roche), Insectin TMPlus (InVitrogen) and Tfx™-20 (Promega). Each of these reagents, used according to the vendor's instructions, permits the introduction of nucleic acid vectors encoding an IDFP to insect cells. Expression vectors optimized for insect cell expression are widely known and are commercially available from, for example, Clontech and InVitrogen. These include both plasmid-based vectors and baculovirus vectors. Insect cell expression vectors are described in detail in "*Baculovirus Expression Vectors*", D. R. O'Reilly, L. K. Miller & V. A. Luckow (1992, W. H. Freeman Co., New York).

Following transfection with an IDFP-encoding vector of the invention, eukaryotic (preferably, but not necessarily mammalian) cells successfully incorporating the construct (intra or extrachromosomally) may be selected, as noted above, by either treatment of the transfected population with a selection agent, such as an antibiotic whose resistance gene is encoded by the vector, or by direct screening using, for example, FACS of the cell population or fluorescence scanning of adherent cultures. Frequently, both types of screening may be used, wherein a negative selection is used to enrich for cells taking up the construct and FACS or fluorescence scanning is used to further enrich for cells expressing IDFPs or to identify specific clones of cells, respectively. For example, a negative selection with the neomycin analog G418 (Life Technologies, Inc.) may be used to identify cells that have received the vector, and fluorescence scanning may be used to identify those cells or clones of cells that express an IDFP to the greatest extent.

4. Modification of Nucleotide Sequences to Enhance Translation of IDFPs.

In many applications it will be advantageous to enhance the expression of fluorescent proteins derived from marine invertebrates or bacteria by modifying the codons in the coding sequences to make them more compatible with codon usage in higher eukaryotes, such as mammals and humans. The methods for this so-called "humanizing" are known in the art and, as noted above, have been applied to *A. victoria* GFP and mutants thereof (U.S. Pat. Nos. 6,020,192 and 5,874,304). Humanization is accomplished by site-directed mutagenesis of the less favored codons to more highly favored codons for the same amino acid, as described herein or as known in the art. The preferred codons for human gene expression are listed in Table 1. The codons in the table are arranged from left to right in descending order of relative use in human genes. In particular, those codons underlined in the table are almost never used in known human genes and, if found in a sequence to be humanized, would therefore represent the most important codons to modify for enhanced expression efficiency in mammalian or human cells. A sequence is considered "humanized" if the codon for one or more amino acids has been changed from the native codon sequence to a codon sequence more favored for translation in human or mammalian cells, preferably without altering the polypeptide coding sequence. Site-directed mutagenesis is well known in the art and is often performed using commercially available kits, such as the EXSITE™ (Catalog No. 200502), QUIKCHANGE™ (Catalog No. 200518) or CHAMELEON® mutagenesis kits (Catalog No. 200509), available from Stratagene.

TABLE 1

PREFERRED DNA CODONS FOR HUMAN USE

| Amino Acids | | | Codons Preferred in Human Genes |
|---|---|---|---|
| Alanine | Ala | A | GCC GCT GCA GCG |
| Cysteine | Cys | C | TGT TGT |
| Aspartic acid | Asp | D | GAC GAT |
| Glutamic acid | Glu | E | GAG GAA |
| Phenylalanine | Phe | F | TTC TTT |
| Glycine | Gly | G | GGC GGG GGA GGT |
| Histidine | His | H | CAC CAT |
| Isoleucine | Ile | I | ATC ATT ATA |
| Lysine | Lys | K | AAG AAA |
| Leucine | Leu | L | CTG TTG CTT <u>CTA TTA</u> |
| Methionine | Met | M | ATG |
| Asparagine | Asn | N | AAC AAT |
| Proline | Pro | P | CCC CCT CCA CCG |
| Glutamine | Gln | Q | CAG CAA |
| Arginine | Arg | R | CGC AGG CGG AGA CGA CGT |
| Serine | Ser | S | AGC TCC TCT AGT TCA TCG |
| Threonine | Thr | T | ACC ACA ACT ACG |
| Valine | Val | V | GTG GTC GTT <u>GTA</u> |
| Tryprophan | Trp | W | TGG |
| Tyro-sine | Tyr | Y | TAC TAT |

The codons at the left represent those most preferred for use in human genes, with human usage decreasing towards the right. Underlined codons are almost never used in human genes.

5. Purification of Intramolecular Dimer Fluorescent Proteins.

Recombinant fluorescent proteins can be purified from bacteria as follows. Bacteria transformed with a recombinant IDFP-encoding vector of the invention are grown in Luria-Bertani medium containing the appropriate selective antibiotic (e.g., ampicillin at 50 $\mu$g/ml). If the vector permits, recombinant polypeptide expression is induced by the addition of the appropriate inducer (e.g., IPTG at 1 mM). Bacteria are harvested by centrifugation and lysed by freeze-thaw of the cell pellet. Debris is removed by centrifugation at 14,000× g, and the supematant is loaded onto a Sephadex G-75 (Pharmacia, Piscataway, N.J.) column equilibrated with 10 mM phosphate buffered saline, pH 7.0. Fractions containing IDFP are identified by fluorescence emission at the expected wavelength when excited by light in the excitation wavelength.

If necessary, IDFPs can be isolated from eukaryotic cells by methods well known to those skilled in the art. It is also contemplated that IDFPs will include a marker or affinity tag sequence to permit affinity purification. Examples include 6×-His, glutathione *S transferase* (GST), or epitope tags such as Flag or the Myc tag. These tags are useful for both bacterial and eukaryotic cell expression and purification of IDFPs.

6. Candidate Modulators.

A candidate modulator or candidate agent being evaluated for a modulatory function on a given interaction or biological process may be a synthetic compound, a mixture of compounds, or may be a natural product (e.g. a plant extract or culture supernatant).

Candidate agents from large, libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Useful candidate compounds may be found within numerous chemical classes. Such compounds may be organic compounds, or small organic compounds. Small organic compounds have a molecular weight of more than 50 yet less than about 2,500 Daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

Candidate agents will be effective at varying concentrations, depending on the nature of the agent and on the nature of its interaction with the polypeptide or polypeptide fragment of interest. Therefore, candidate agents should be screened at varying concentrations. Generally, concentrations from about 10 mM to about 1 fM are preferred for screening. The association constants of agents that bind polypeptides or fragments thereof will generally be in the range of about 1 mM to about 1 fM, and optimally in the range of about 1 $\mu$M to about 1 pM or less.

Uses of Intramolecular Dimer Fluorescent Proteins According to the Invention

IDFPs can be used in any application for which fluorescent proteins are suited. For example, IDFPs can be used as reporter genes to monitor the activity of promoter sequences, to investigate the cellular localization of fusion proteins, to mark cellular proteins for FACS analyses of cell populations, to monitor viral vector infection, to monitor transgene expression in vivo or in culture, and to monitor protein:protein interactions both in vivo and in vitro. It is also expected that IDFPs comprising fluorescent proteins whose spectral characteristics are sensitive to intracellular or extracellular environmental changes (e.g., pH, redox. status, phosphorylation of the fluorescent protein, etc.) will continue to be sensitive to those changes in the context of an IDFP. Because IDFPs do not heterodimerize, they are particularly well suited for multiple-labeling studies involving the co-expression of IDFP-fusion proteins with differing spectral characteristics. Techniques useful for the detection of IDFP fusion proteins include, for example, standard fluorescent microscopy, confocal microscopy, flow cytometry and fluorescence activated cell sorting (FACS).

As noted, IDFPs are particularly well suited to applications that rely on FRET. The lack of heterodimerization between IDFPs with differing spectral characteristics that permit FRET but that share the same dimerization interfaces is a major improvement over previous methods using fluorescent proteins that could heterodimerize, since it removes a significant source of FRET background. In one embodiment, two different IDFPs that have overlapping emission and excitation spectra (i.e., they are donor and acceptor to each other) are used to generate fusions with two different cellular (or viral) proteins or protein domains being investigated for their ability to interact. A specific interaction of the fusion partners will result in a change in the detected emission spectrum from that of the donor to that of the acceptor when a mixture of the two IDFP fusion proteins is irradiated with light that excites the donor fluorophore. This type of assay is readily adapted to a screening format, in which known interactors are exposed to candidate compounds. Detection of a change from the acceptor's emission profile to the donor's emission profile indicates that a candidate compound has disrupted the interaction between the fusion partners. Either of these assays can be performed in vivo or in vitro. An example of a donor/acceptor fluorescent protein pair is P4-3 and S65C or S65T (Table 2; U.S. Pat. No. 5,981,200). Other examples of donor/acceptor pairs of fluorescent polypeptides include, but are not limited to any of S72A, K79R, Y145F, M153A and T2031 (excitation λ 395 =m., emission λ 511 nm) as donor, and any of S65G, T203Y (excitation λ 514 nm, emission λ 527 nm) or T203Y/S65G, V68L or Q69K (excitation λ 515 nm, emission λ 527 nm) as acceptor (See Tsien et al., WO 97/28261). Each of these proteins shares the dimerization interface of *A. victoria* GFP. Their expression as IDFPs would allow their co-expression without heterodimerization.

Figure 5:
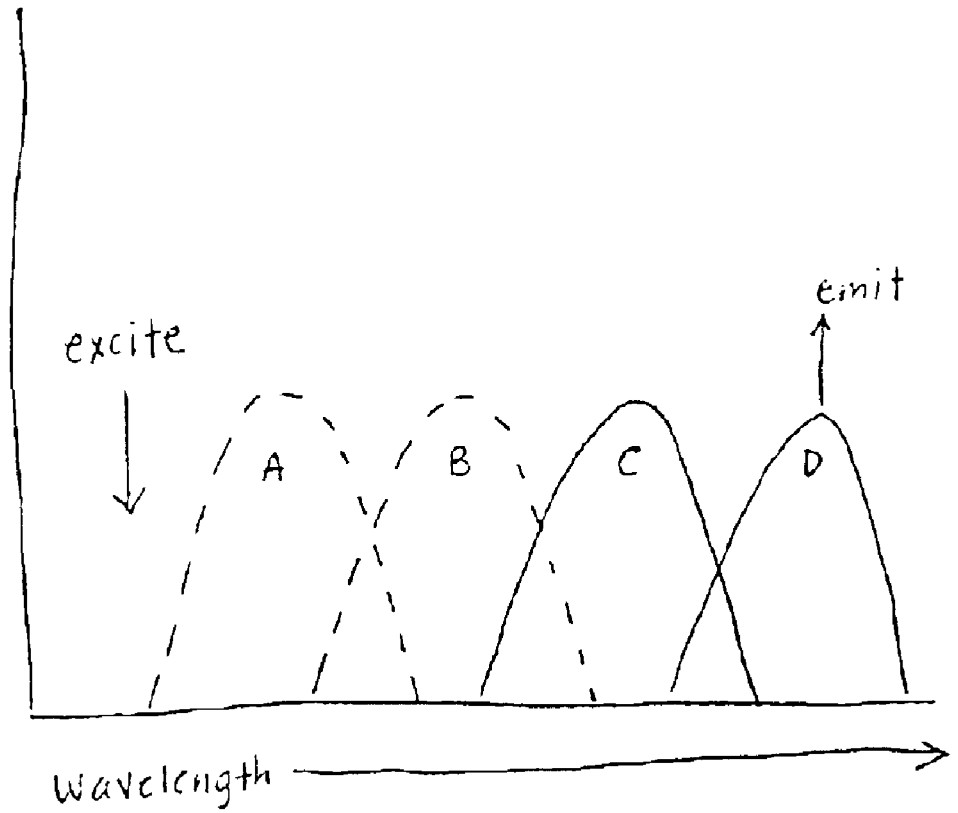
FIG. 5 shows relationships between emission and excitation peaks for donor and acceptor fluorophores capable of FRET.

A pair of fluorescent proteins that are useful according to the invention function as fluorescent donor and fluorescent acceptor, respectively, in the context of fluorescence resonance energy transfer. The ability of a pair of fluorescent proteins to function as fluorescent donor and fluorescent acceptor, respectively, in the context of fluorescence resonance energy transfer, is determined experimentally and is influenced by a number of factors including donor/acceptor peaks, emission/excitation peaks, peak widths, the efficiency of energy transfer within a fluorescent moiety and peak overlap. Preferably, 1) the donor excitation peak, A, FIG. 5, will overlap minimally with the acceptor excitation peak, C, FIG. 5, such that excitation of the' donor does not excite the acceptor; 2) the donor excitation peak, A, FIG. 5, and the donor emission peak, B, FIG. 5, have sufficient overlap to permit efficient energy transfer; 3) the donor emission peak, B, FIG. 5, and the acceptor excitation peak, C, FIG. 5, have sufficient overlap to permit efficient FRET energy transfer; 4) the donor emission peak, B, FIG. 5 and the acceptor emission peak, D, FIG. 5 have sufficient overlap to allow for differentiation between FRET and non-FRET energy transfer; and 5) the donor excitation peak, A, FIG. 5 and the acceptor emission peak, D, FIG. 5 have sufficient overlap to allow for differentiation between FRET and non-FRET energy transfer.

Generally, an acceptable donor/acceptor pair exhibits ≧50% quenching of donor emission at a chromophore distance of ≧10 Å. This is based on the Förster radius, $R_o$, which is the distance at which 50% of excited donors are deactivated by FRET (i.e., distance at which energy transfer is 50% efficient). The value of $R_o$ is dependent on the spectral properties of the donor and acceptor fluorophores, with a general formula: $R_o=[8.8\times10^{23}\cdot\kappa^2\cdot n^{-4}\cdot QY_D\cdot J(\lambda)]^{1/6}$ Å, where $\kappa^{2-}$ dipole orientation factor (0–4; $\kappa^2$=2/3 for randomly oriented dono acceptors); $QY_D$=the quantum yield of the donor in the absence of the acceptor; n=the refractive index; and J(λ)=the spectral overlap integral (the shared area under the overlapping donor emission and acceptor excitation peaks).

The advantage resulting from the forced intramolecular homodimer formation is most apparent when, for example, fluorescent proteins with different emission characteristics, derived from the same parent fluorescent protein, are expressed in a single cell. For example, if two variants of *R. reniformis* GFP have spectral characteristics that permit FRET between the variants, both of these proteins will have the same dimerization interfaces. Without the forced homodimerization occurring in an IDFP, the background level of acceptor fluorescence upon irradiation within the donor's excitation spectrum will be higher than if IDFP versions of the same fluorescent proteins are used.

Even if FRET does not occur between differing fluorescent proteins that share the same dimerization interface, heterodimerization between two fluorescent fusion proteins via that interface can be a problem. For example, such heterodimerization can reduce the sensitivity of sub-cellular localization studies using two labels. Heterodimerization will segregate the labeled proteins into three populations: homodimers of the first fusion protein, homodimers of the second fusion protein, and heterodimers comprising both. Even if one assumes, strictly for the sake of argument, that the heterodimerization will not affect the intracellular localization of the proteins, heterodimer formation will reduce the amount of either homodimer available to segregate to a given location in the cell. This will result in decreased sensitivity in the assay. Therefore, the use of IDFPs in such a situation will improve upon detection sensitivity even if one is not relying upon FRET for detection.

EXAMPLES

Example 1

Monitoring the Interaction of Polypeptides Using IDFPs

IDFPs are well suited for applications that monitor the association of fusion polypeptides using energy transfer. In order to monitor the association of two polypeptides of interest using IDFPs, one must first select a pair of fluorescent polypeptides that are donor and acceptor to each other. Each polypeptide in the pair must be capable of homodimerization. An example of such a pair P4-3 and S65T. Another pair useful according to the invention is P4-3 and *R. reniformis* GFP (hrGFP). The nucleic acid sequence encoding the fluorescence donor polypeptide is used to generate a construct encoding, in order, a copy of the donor polypeptide (e.g., P4-3), a linker, a second copy of the fluorescence donor polypeptide and one of the polypeptides of interest (alternatively, the sequence encoding the protein of interest may be placed upstream of and in frame with the sequences encoding the IDFP). Similarly, the sequence encoding the fluorescence acceptor polypeptide is used to generate a construct encoding, in order, a copy of the acceptor polypeptide (e.g., S65T), a linker, a second copy of the fluorescence acceptor polypeptide and the second polypeptide of interest (alternatively, the sequence encoding the protein of interest may be placed upstream of and in frame with the sequences encoding the acceptor IDFP). An example of a pair of proteins of interest is the Ras proto-oncogene product and the Raf-1 kinase. The G-Protein Ras binds to Raf-1 in response to signals originating at receptor tyrosine kinases. A human c-Ha-Ras cDNA sequence is available at GenBank Accession No. J00277, and a human Raf-1 kinase sequence is available at GenBank Accession No. NM002880. As an example, Ras coding sequences may be ligated in frame to the donor P4-3 IDFP construct, and the Raf-1 coding sequences may be ligated in frame to the acceptor S65A IDFP construct.

Constructs encoding the two IDFP-fusion proteins are transfected, either simultaneously or sequentially into cells in which the protein:protein interaction is to be studied (e.g., HeLa cells, NIH3T3 cells, or another specific cell type of interest) using methods well known in the art (e.g., lipofection, electroporation, calcium phosphate precipitation, or even retroviral infection following generation of recombinant retroviral vector particles as known in the art).

After selection of cells incorporating and expressing the constructs by standard methods, the interaction of the proteins of interest is measured by detection of fluorescent emission upon irradiation with light that excites the donor fluorophore, in this instance P4-3, but not the acceptor fluorophore, S65T. If the fused Ras and Raf-1 domains interact, excitation with 381 nm light will result in energy transfer between the P4-3 and S65T fluorophores and emission of light with a maximum at about 511 nm. In contrast, if the domains do not interact, the emission maximum upon excitation at 381 nm will be at about 445 nm, the emission maximum of P4-3. This therefore allows the monitoring of the interaction of the two domains in response to stimuli, such as the addition of growth factor, growth factor analogs, or candidate modulators of the signal transduction pathway.

The protein:protein interaction assay using IDFP fusion proteins described above may also be performed in vitro with isolated or purified IDFP fusion proteins. This type of assay, or even the cell-based assay described above may be readily adapted to a high-throughput format by placing the transfected cells or protein samples in a multiwell container and monitoring fluorescence output of samples exposed to various candidate modulators. Further, by performing the interaction assay in the presence or absence of a candidate modulator, one may adapt the method for screening of candidate modulator compounds to identify compounds that either increase or decrease the measured interaction. A change in the interaction in the presence of a candidate modulator relative to the interaction in its absence is indicative of a modulatory effect.

Example 2

Labeling a Cell with an IDFP

IDFPs according to the invention can be used in any application in which fluorescent polypeptides are useful. For example, cells can be labeled by expression of IDFPs to monitor the uptake and expression of transgene constructs, including plasmid-based and retroviral constructs. Cells may also be labeled to facilitate subsequent FACS analysis in a mixed population. To label a cell, an IDFP-encoding construct is introduced to cells by standard methods appropriate to that cell type. Following introduction, selection for cells receiving the construct can either be performed by standard positive or negative selection based on additional selectable marker sequences (e.g., antibiotic resistance genes), by sorting or selection by FACS, or by allowing cells to form colonies and isolating those colonies that fluoresce when irradiated with light within the excitation spectrum of the IDFP. Maintaining the cells under conditions permitting the expression of the IDFP will permit the detection of the cells by fluorescence.

Example 3

Double Label Monitoring of Protein Localization

Fluorescently labeled proteins are often used to examine the sub-cellular localization of proteins of interest. Frequently, it is useful to monitor the localization of two or more proteins or protein domains simultaneously, for example, as a means of identifying relationships between the proteins. When two or more proteins are labeled with fluorescent polypeptides that have the capacity to heterodimerize, the sensitivity of the localization assay can be adversely affected by heterodimerization between the fluorescent polypeptides.

Examples of proteins to be monitored for localization include proteins that are recruited to the vicinity of the plasma membrane upon a stimulus such as growth factor engagement of a receptor (e.g., G-proteins, Protein Kinase A, SH2-domain containing proteins, etc.), proteins that localize to the nucleus in response to a stimulus (e.g., steroid hormone receptor), or proteins that localize to the golgi, mitochondria, nuclear pores or any other subcellular locale.

In order to simultaneously monitor the localization of two proteins of interest, two IDFP fusion constructs, each comprising sequences encoding one of the proteins of interest, are introduced to cells, either simultaneously or sequentially, using standard methods appropriate for that cell type. The localization of the IDFP-tagged proteins is monitored by fluorescence microscopy using excitation wavelengths and filter sets appropriate for the different fluorophores. While not wishing to exclude the possibility, it is generally not necessary that the two IDFPs be fluorescent donor and acceptor to each other. More frequently, unless one is assaying for direct interaction of the proteins, it is preferred that the fluorescent proteins are not related to each other in this manner. The IDFP fusion protein constructs are made using standard methods well known in the art. Examples of pairs of fluorescent polypeptides that are well suited for simultaneous monitoring of localization include, but are not limited to any of S72A, K79R, Y145F, M153A and T2031 (excitation λ 395 nm, emission λ 511 nm) as donor, and any of S65G, T203Y (excitation λ 514 nm, emission λ 527 nm) or T203Y/S65G, V68L or Q69K (excitation λ 515 nm, emission λ 527 nm) as acceptor (See Tsien et al., WO 97/2826 1). See also Table 2.

TABLE 2

FLUORESCENCE CHARACTERISTICS OF VARIOUS GFP MUTANTS

| Clone | Mutation(s) | Excitatin max (nm) | Emission max (nm) | Extinct. Coefficienqt ($M^{-1}cm^{-1}$) | | Quantum Yield |
|---|---|---|---|---|---|---|
| Wild type | None | 393 (475) | 508 | 21,000 | (7,150) | 0.77 |
| P4 | Y66H | 383 | 447 | 13,500 | | 0.21 |
| P4-3 | Y66H<br>Y145F | 381 | 445 | 14,000 | | 0.38 |
| W-7 | Y66W<br>N146L<br>M153T<br>V163A<br>N212K | 433 (453) | 475 (501) | 18,000<br>(17,100) | | 0.67 |

TABLE 2-continued

FLUORESCENCE CHARACTERISTICS OF VARIOUS GFP MUTANTS

| Clone | Mutation(s) | Excitatin max (nm) | Emission max (nm) | Extinct. Coefficienqt ($M^{-1}cm^{-1}$) | | Quantum Yield |
|---|---|---|---|---|---|---|
| W2 | Y66W<br>I123V<br>Y145H<br>H148R<br>M153T<br>V163A<br>N212K | 432 (453) | 480 | 10,000 | (9,600) | 0.72 |
| S65T | S65T | 489 | 511 | 39,200 | | 0.68 |
| P4-I | S65T<br>M153A<br>K238E | 504 (396) | 514 | 14,500 | (8,600) | 0.53 |
| S65A | S65A | 471 | 504 | | | |
| S65C | S65C | 479 | 507 | | | |
| S65L | S65L | 484 | 510 | | | |
| Y66F | Y66F | 360 | 442 | | | |
| Y66W | Y66W | 458 | 480 | | | |
| 10c | S65G<br>V68L<br>V72A<br>T203Y | 513 | 527 | | | |
| W1B | F64L<br>S65T<br>Y66W<br>N146I<br>M153T<br>V163A<br>N212K | 432 (453) | 476 (503) | | | |
| Emerald | S65T<br>S72A<br>N149K<br>M153T<br>I167T | 487 | 508 | | | |
| Sapphire | S72A<br>Y145F<br>T203I | 395 | 511 | | | |

What is claimed is:

1. A recombinant fusion polypeptide comprising a first and a second polypeptide, wherein:

a) said first polypeptide is peptide bonded to said second polypeptide via a linker sequence of 5 to 50 amino acids in length, b) said first and said second polypeptides are monomers of a multimeric fluorescent protein, and said first and said second polypeptides are not fluorescent donor and acceptor to each other; and c) said recombinant fusion polypeptide is fluorescent when excited.

2. The recombinant fusion polypeptide of claim 1, further comprising a third polypeptide peptide bonded to said recombinant fusion polypeptide.

3. The recombinant fusion polypeptide of claim 2 wherein said third polypeptide is a member of a specific binding pair.

4. The recombinant fusion polypeptide of claim 2 wherein said third polypeptide is fused to the amino terminus of said first polypeptide.

5. The recombinant fusion polypeptide of claim 2 wherein said third polypeptide is fused to the carboxy terminus of said second polypeptide sequence.

6. The recombinant fusion polypeptide of claim 1 wherein each of said first and said second polypeptide, independently, is a monomer of a multimeric protein selected from the group consisting of: *R. reniformis* GFP, *R. mulleri* GFP and *A. victoria* GFP.

7. The recombinant fusion polypeptide of claim 1 wherein both of said first and second polypeptides are monomers of a single multimeric protein selected from the group consisting of *R. reniformis* GFP, *R. mulleri* GFP and *A. victoria* GFP.

8. A pair of polypeptides, one member of said pair comprising a polypeptide labeled with a fluorescent dye, and the other member of said pair comprising a recombinant fusion polypeptide, said fusion polypeptide comprising a first and a second polypeptide, wherein:

a) said first polypeptide is peptide bonded to said second polypeptide via a linker sequence, b) said first and said second polypeptides are monomers of a multimeric fluorescent protein, and said first and said second polypeptides are not fluorescent donor and acceptor to each other; and c) said recombinant fusion polypeptide is fluorescent when excited;

wherein said fluorescent dye and said recombinant fusion polypeptide are fluorescent donor and acceptor to each other.

9. A pair of recombinant fusion polypeptides comprising a) a first fusion polypeptide comprising a first and a second polypeptide, wherein:

i) said first polypeptide is peptide bonded to said second polypeptide via a linker sequence, ii) said first and said second polypeptides are monomers of a multimeric fluorescent protein, and said first and said second polypeptides are not fluorescent donor and acceptor to each other; and iii) said recombinant fusion polypeptide is fluorescent when excited; and b) a second fusion polypeptide comprising a first and a second polypeptide, wherein:

i) said first polypeptide is peptide bonded to said second polypeptide via a linker sequence, ii) said first and said second polypeptides are monomers of a multimeric fluorescent protein, and said first and said second polypeptides are not fluorescent donor and acceptor to each other; and iii) said recombinant fusion polypeptide is fluorescent when excited; wherein said first fusion polypeptide of (a) and said second fusion polypeptide of (b) are fluorescent donor and acceptor to each other.

10. The pair of recombinant fusion polypeptides of claim 9 wherein each of said first and second fusion polypeptides further comprises a third polypeptide, and wherein said third polypeptide of said first fusion polypeptide comprises a sequence which is different from said third polypeptide of said second fusion polypeptide.

11. A method of monitoring the interaction of two polypeptides of interest, said method comprising the steps of:

(a) contacting a first polypeptide and a second polypeptide wherein:

(i) said first polypeptide is a recombinant fusion polypeptide of claim 4 wherein said third polypeptide is a first polypeptide of interest;

(ii) said second polypeptide comprises a second polypeptide of interest and is fluorescently labeled; and (iii) the fluorophores comprised by said first and second polypeptides are fluorescent donor and fluorescent acceptor to each other;

(b) exciting said donor fluorophore; and (c) detecting fluorescent emission from said fluorescent acceptor, wherein said emission is indicative of the interaction of said first and said second polypeptides of interest.

12. The method of claim 11 wherein said second polypeptide comprises a fusion polypeptide of claim 5, wherein said third polypeptide of said second fusion polypeptide is different from said third polypeptide of said first fusion polypeptide.

13. The method of claim 11 wherein said contacting step is performed in vitro.

14. The method of claim 11 wherein said contacting step is performed in a cell.

15. The method of claim 14 wherein said contacting comprises the step of introducing nucleic acid encoding said first and said second polypeptides to a cell.

16. A method of screening for a compound that modulates the interaction of a first and a second member of a specific binding pair, said method comprising the steps of:

(a) contacting a first polypeptide and a second polypeptide in the presence and absence of a candidate modulator wherein:

(i) said first polypeptide is a recombinant fusion polypeptide of claim 5, wherein said member of a specific binding pair is said first member of a specific binding pair;

(ii) said second polypeptide is fluorescently labeled and comprises said second member of a specific binding pair; and (iii) the fluorophores comprised by said first and second polypeptides are fluorescent donor and, acceptor to each other;

(b) exciting said donor fluorophore; and (c) detecting the fluorescence of said acceptor fluorophore, wherein emission of the spectrum characteristic of said fluorescent acceptor indicates the interaction of said first and said second members of said specific binding pair, and wherein a change in said interaction in the presence of said candidate modulator indicates that said candidate modulator modulates the interaction of the members of said specific binding pair.

17. The method of claim 16 wherein said second polypeptide is a recombinant fusion polypeptide of claim 5 and said member of a specific binding pair comprised by said second polypeptide is said second member of a specific binding pair.

18. A recombinant fusion polypeptide comprising a first and a second polypeptide, wherein:

a) said first polypeptide is peptide bonded to said second polypeptide via a linker sequence selected from the group consisting of (Arg-Ala-Arg-Asp-Pro-Arg-Val-Pro-Val-Ala-Thr)$_{1-5}$ (SEQ ID NO: 8, 69–72), (Gly-Ser)$_{1-15}$ (SEQ ID NO: 9–23), (Thr-Ser-Pro)$_{1-15}$ (SEQ ID NO: 24–38), (Gly-Gly-Gly)$_{1-15}$ (SEQ ID NO: 39–53), (Glu-Lys)$_{1-15}$ (SEQ ID NO: 54–68), and (Gly$_4$Ser)$_{2-4}$ (SEQ ID NO: 5–7);

b) said first and said second polypeptides are monomers of a multimeric fluorescent protein, and said first and said second polypeptides are not fluorescent donor and acceptor to each other; and c) said recombinant fusion polypeptide is fluorescent when excited.

* * * * *

UNITED STATES PATENT AND TRADEMARK OFFICE

CERTIFICATE OF CORRECTION

PATENT NO. : 6,936,428 B2
DATED : August 30, 2005
INVENTOR(S) : Davis et al.

It is certified that error appears in the above-identified patent and that said Letters Patent is hereby corrected as shown below:

Title page,
Item [54], Title, replace the word "FLOURESCENT" with the word -- FLUORESCENT --.

Signed and Sealed this

First Day of November, 2005

JON W. DUDAS
*Director of the United States Patent and Trademark Office*